US012599584B2

(12) United States Patent
Weinstock-Rosin et al.

(10) Patent No.: US 12,599,584 B2
(45) Date of Patent: Apr. 14, 2026

(54) INDOLINE DERIVATIVES, COMPOSITIONS COMPRISING THEM AND USES THEREOF

(71) Applicants: Yissum Research Development Company of The Hebrew University of Jerusalem Ltd., Jerusalem (IL); BAR ILAN UNIVERSITY, Ramat Gan (IL)

(72) Inventors: Marta Weinstock-Rosin, Jerusalem (IL); Abraham Nudelman, Rehovot (IL); Shani Zeeli, Ness Ziona (IL)

(73) Assignees: Yissum Research Development Company of The Hebrew University of Jerusalem Ltd., Jerusalem (IL); Bar-Ilan University, Ramat Gan (IL)

( * ) Notice: Subject to any disclaimer, the term of this patent is extended or adjusted under 35 U.S.C. 154(b) by 198 days.

(21) Appl. No.: 16/071,092

(22) PCT Filed: Jan. 19, 2017

(86) PCT No.: PCT/IL2017/050079
§ 371 (c)(1),
(2) Date: Jul. 19, 2018

(87) PCT Pub. No.: WO2017/125932
PCT Pub. Date: Jul. 27, 2017

(65) Prior Publication Data
US 2021/0169850 A1 Jun. 10, 2021

Related U.S. Application Data

(60) Provisional application No. 62/281,313, filed on Jan. 21, 2016.

(51) Int. Cl.
| | |
|---|---|
| *A61K 31/405* | (2006.01) |
| *A61K 31/4045* | (2006.01) |
| *A61P 25/00* | (2006.01) |
| *A61P 29/00* | (2006.01) |

(52) U.S. Cl.
CPC ........ *A61K 31/405* (2013.01); *A61K 31/4045* (2013.01); *A61P 25/00* (2018.01); *A61P 29/00* (2018.01)

(58) Field of Classification Search
CPC .............. A61K 31/405; A61K 31/4545; A61K 31/4045; C07D 208/08; C07D 208/14; C07D 208/18; C07D 209/08; C07D 209/14; C07D 209/18; A61P 25/00; A61P 29/00
See application file for complete search history.

(56) References Cited

U.S. PATENT DOCUMENTS

| | | | |
|---|---|---|---|
| 5,206,240 A | 4/1993 | Baldwin et al. | |
| 6,002,018 A | 12/1999 | Terranova et al. | |
| 6,380,238 B1 | 4/2002 | Adams et al. | |
| 2003/0207915 A1* | 11/2003 | Cheng ........................ | A61P 9/10 |
| | | | 514/307 |
| 2010/0292193 A1* | 11/2010 | McBride .............. | A61K 31/407 |
| | | | 514/152 |
| 2011/0112148 A1 | 5/2011 | Falco et al. | |
| 2011/0268653 A1* | 11/2011 | Negrete ............... | A61K 31/505 |
| | | | 424/9.1 |

FOREIGN PATENT DOCUMENTS

| | | | |
|---|---|---|---|
| CN | 101878200 A | | 11/2010 |
| JP | 2008149213 A | * | 7/2008 |
| RU | 2387640 C1 | * | 4/2010 |
| WO | WO 2001/040183 A1 | | 6/2001 |
| WO | WO 2013/150529 A2 | | 10/2013 |
| WO | WO 2015/049667 A1 | | 4/2015 |

OTHER PUBLICATIONS

RU 2387640 C1 (publ. Apr. 27, 2010), English translation (Year: 2010).*
Elder et al., J. Pharmacy & Pharmacology, vol. 61, pp. 269-278, publ. 2009 (Year: 2009).*
National Library of Medicine, publ. Mar. 17, 2015, pp. 1-8 (Year: 2015).*
Mori et. al., English translation of JP 2008149213, publ. Jul. 3, 2008, pp. 1-13 (Year: 2008).*
Adler, S. et al. (2013). Induction of severe systemic lupus erythematosus by TNF blockade and response to anti-IL-6 strategy. Journal of allergy and clinical immunology, 131(4), 1235-1237.
Allez, M. et al. (2010). Report of the ECCO pathogenesis workshop on anti-TNF therapy failures in inflammatory bowel diseases: definitions, frequency and pharmacological aspects. Journal of Crohn's and Colitis, 4(4), 355-366.
Amundsen, L. H. et al. (1951). Reduction of nitriles to primary amines with lithium aluminum hydride1. Journal of the American Chemical Society, 73(1), 242-244.
Astil, B. et al. (1958). A Synthesis of 5-Ketolilolidine. The Journal of Organic Chemistry, 23(2), 316-318.
Baumann, H. et al. (1994). The acute phase response. Immunology today, 15(2), 74-80.
Ben-Horin, S. et al. (2014). Tailoring anti-TNF therapy in IBD: drug levels and disease activity. Nature reviews Gastroenterology & hepatology, 11(4), 243-255.
Berge, S. M. et al. (1977). Factors That Impact the Developability of Drug Candidates: An Overview. J. Pharm. Sci, 66, 1-19.
Berney, T. et al. (1999). Serum profiles of interleukin-6, interleukin-8, and interleukin-10 in patients with severe and mild acute pancreatitis. Pancreas, 18(4), 371-377.
Bongartz, T. et al. (2006). Anti-TNF antibody therapy in rheumatoid arthritis and the risk of serious infections and malignancies: systematic review and meta-analysis of rare harmful effects in randomized controlled trials. Jama, 295(19), 2275-2285.

(Continued)

*Primary Examiner* — Sarah Pihonak
(74) *Attorney, Agent, or Firm* — Mark S. Cohen; PEARL COHEN ZEDEK LATZER BARATZ LLP

(57) ABSTRACT

The present invention is directed to indoline derivatives and salts thereof, compositions comprising them and uses thereof for the treatment of diseases and disorders associated with at least one of oxidative stress, an immune response, release of NO and release of pro-inflammatory cytokine.

1 Claim, 16 Drawing Sheets

(56)            References Cited

OTHER PUBLICATIONS

Cai, L. et al. (2011). Palladium-catalyzed Coupling between Aryl Halides and Trimethylsilylacetylene Assisted by Dimethylaminotrimethyltin. Chinese Journal of Chemistry, 29(5), 1059-1062.

Chiquetto Paracatu, L. et al. (2014). Alkyl caffeates as anti-helicobacter pylori and scavenger of oxidants produced by neutrophils. Medicinal Chemistry, 10(1), 74-80.

Cornu, M. et al. (2013). mTOR in aging, metabolism, and cancer. Current opinion in genetics & development, 23(1), 53-62.

DeFuria, J. et al. (2013). B cells promote inflammation in obesity and type 2 diabetes through regulation of T-cell function and an inflammatory cytokine profile. Proceedings of the National Academy of Sciences, 110(13), 5133-5138.

DellaGioia, N. et al. (2013). Bupropion pre-treatment of endotoxin-induced depressive symptoms. Brain, behavior, and immunity, 31, 197-204.

Dhir, A. et al. (2007). Involvement of l-arginine-nitric oxide-cyclic guanosine monophosphate pathway in the antidepressant-like effect of venlafaxine in mice. Progress in Neuro-Psychopharmacology and Biological Psychiatry, 31(4), 921-925.

Dias, V. et al. (2013). The role of oxidative stress in Parkinson's disease. Journal of Parkinson's disease, 3(4), 461-491.

Dinarello, C. A. (1997). Proinflammatory and anti-inflammatory cytokines as mediators in the pathogenesis of septic shock. Chest, 112(6), 321S-329S.

Finkin-Groner, E. et al. (2017). Indoline derivatives mitigate liver damage in a mouse model of acute liver injury. Pharmacological Reports, 69(5), 894-902.

Glennon, R. A. et al. (1984). Synthesis and evaluation of a novel series of N, N-dimethylisotryptamines. Journal of medicinal chemistry, 27(1), 41-45.

Gonzalez-Juanatey, C. et al. (2012). Anti-TNF-alpha-adalimumab therapy is associated with persistent improvement of endothelial function without progression of carotid intima-media wall thickness in patients with rheumatoid arthritis refractory to conventional therapy. Mediators of inflammation, 2012.

Hajjar, D. P. et al. (2013). Biological relevance of inflammation and oxidative stress in the pathogenesis of arterial diseases. The American journal of pathology, 182(5), 1474-1481.

Hunt, R. R. et al. (1966). A new synthesis of methoxyindoles. Journal of the Chemical Society C: Organic, 344-345.

International Search Report issued for PCT Application No. PCT/IL2017/050079 dated May 22, 2017.

Irony-Tur-Sinai, M. et al. (2006). Amelioration of autoimmune neuroinflammation by recombinant human alpha-fetoprotein. Experimental neurology, 198(1), 136-144.

Kanasaki, K. et al. (2013). Diabetic nephropathy: the role of inflammation in fibroblast activation and kidney fibrosis. Frontiers in endocrinology, 4, 7.

Lang, U. E. et al. (2013). Molecular mechanisms of depression: perspectives on new treatment strategies. Cellular Physiology and Biochemistry, 31(6), 761-777.

Levitt, J. E. et al. (Aug. 2006). Treatment of acute lung injury: historical perspective and potential future therapies. In Seminars in respiratory and critical care medicine (vol. 27, No. 04, pp. 426-437). Copyright © 2006 by Thieme Medical Publishers, Inc., 333 Seventh Avenue, New York, NY 10001, USA.

Maes, M. (1999). Major depression and activation of the inflammatory response system. Cytokines, stress, and depression, 25-46.

Maes, M. (2013). Inflammatory and oxidative and nitrosative stress cascades as new drug targets in myalgic encephalomyelitis and chronic fatigue syndrome. Inflammation in Psychiatry, 28, 162-174.

Magro, F. et al. (2010). Management of inflammatory bowel disease with infliximab and other anti-tumor necrosis factor alpha therapies. BioDrugs, 24(1), 3-14.

Mandell, B. F. et al. (2014). The role of TNF inhibitors in psoriatic disease. Semin Cutan Med Surg, 33(4 Suppl), 64-68.

Mangialasche, F. et al. (2009). Biomarkers of oxidative and nitrosative damage in Alzheimer's disease and mild cognitive impairment. Ageing research reviews, 8(4), 285-305.

Martínez-Castelao, A. et al. (2015). The concept and the epidemiology of diabetic nephropathy have changed in recent years. Journal of clinical medicine, 4(6), 1207-1216.

McInnes, I. B. et al. (2007). Cytokines in the pathogenesis of rheumatoid arthritis. Nature Reviews Immunology, 7(6), 429-442.

Muyderman, H. et al. (2014). Mitochondrial dysfunction in amyotrophic lateral sclerosis-a valid pharmacological target?. British journal of pharmacology, 171(8), 2191-2205.

Nakamura, Y. et al. (2015). A formal anti-Markovnikov hydroamination of allylic alcohols via tandem oxidation/1, 4-conjugate addition/1, 2-reduction using a Ru catalyst. Chemical Communications, 51(35), 7459-7462.

Nazıroğlu, M. et al. (2012). Role of oxidative stress and Ca 2+ signaling on molecular pathways of neuropathic pain in diabetes: focus on TRP channels. Neurochemical research, 37(10), 2065-2075.

Nickoloff, B. J. et al. (2007). Immunopathogenesis of psoriasis. Clinical reviews in allergy & immunology, 33(1-2), 45-56.

Norman, J. (1998). The role of cytokines in the pathogenesis of acute pancreatitis. The American Journal of Surgery, 175(1), 76-83.

Olsson, B. et al. (2013). Microglial markers are elevated in the prodromal phase of Alzheimer's disease and vascular dementia. Journal of Alzheimer's Disease, 33(1), 45-53.

Overwater, I. E. et al. (2015). Epilepsy in children with tuberous sclerosis complex: chance of remission and response to antiepileptic drugs. Epilepsia, 56(8), 1239-1245.

Papageorgiou, G. et al. (2000). Effects of aromatic substituents on the photocleavage of 1-acyl-7-nitroindolines. Tetrahedron, 56(41), 8197-8205.

Park, J. et al. (2015). Mild Rh (III)-catalyzed C7-allylation of indolines with allylic carbonates. The Journal of organic chemistry, 80(3), 1818-1827.

Podolsky, D. K. (2002). Inflammatory bowel disease. New England Journal of Medicine, 347(6), 417-429.

Pradhan, S. et al. (2013). Commentary: progressive inflammation as a contributing factor to early development of Parkinson's disease. Experimental neurology, 241, 148-155.

Raaschou, P. et al. (2013). Rheumatoid arthritis, anti-tumour necrosis factor therapy, and risk of malignant melanoma: nationwide population based prospective cohort study from Sweden. Bmj, 346.

Rapoport, H. et al. (1960). Alkaloids of Geissospermum vellosii. Further Studies on Geissospermine and the Structures of the Indolic Cleavage Products, Geissoschizine1 and Apogeissoschizine. Journal of the American Chemical Society, 82(16), 4404-4414.

Reichert, F. et al. (2003). Complement-receptor-3 and scavenger-receptor-AI/II mediated myelin phagocytosis in microglia and macrophages. Neurobiology of disease, 12(1), 65-72.

Reuter, S. et al. (2010). Oxidative stress, inflammation, and cancer: how are they linked?. Free radical biology and medicine, 49(11), 1603-1616.

Rodrigo, R. et al. (2013). Oxidative stress and pathophysiology of ischemic stroke: novel therapeutic opportunities. CNS & Neurological Disorders-Drug Targets (Formerly Current Drug Targets-CNS & Neurological Disorders), 12(5), 698-714.

Rongioletti, F. et al. (2014). Inflammatory/infectious cutaneous side effects of biological drugs in patients with psoriasis: a general review with personal data. G Ital Dermatol Venereol, 149(3), 311-6.

Roy, S. et al. (2005). Synthesis of 7-keto-Go6976 (ICP-103). Synthetic communications, 35(4), 595-601.

Roy, S. et al. (2006). Synthesis of N-alkyl substituted bioactive indolocarbazoles related to Gö6976. Tetrahedron, 62(33), 7838-7845.

Rubino, M. T. et al. (2011). Identification of novel matrix metalloproteinase inhibitors by screening of phenol fragments library. Archiv der Pharmazie, 344(9), 557-563.

Schmid, R. M. et al. (1999). Cytokines in acute pancreatitis—new pathophysiological concepts evolve. European journal of gastroenterology & hepatology, 11(2), 125-128.

(56) References Cited

OTHER PUBLICATIONS

Schrag, M. et al. (2013). Oxidative stress in blood in Alzheimer's disease and mild cognitive impairment: a meta-analysis. Neurobiology of disease, 59, 100-110.

Schulz, E. et al. (2004). Oxidative stress, antioxidants, and endothelial function. Current medicinal chemistry, 11(9), 1093-1104.

Seror, R. et al. (2013). Pattern of demyelination occurring during anti-TNF-α therapy: a French national survey. Rheumatology, 52(5), 868-874.

Shapiro, S. L. et al. (1959). Aminoalkylamides and Oxazolidinediones1. Journal of the American Chemical Society, 81(12), 3083-3088.

Shirota, O. et al. (2003). Concise large-scale synthesis of psilocin and psilocybin, principal hallucinogenic constituents of "Magic Mushroom". Journal of natural products, 66(6), 885-887.

Smith, K. J. et al. (1999). Demyelination: the role of reactive oxygen and nitrogen species. Brain pathology, 9(1), 69-92.

Smith, M. A. et al. (2005). Chronological primacy of oxidative stress in Alzheimer disease. Neurobiology of aging, 26(5), 579-580.

Song, C. et al. (2009). Imbalance between pro-and anti-inflammatory cytokines, and between Th1 and Th2 cytokines in depressed patients: the effect of electroacupuncture or fluoxetine treatment. Pharmacopsychiatry, 42(05), 182-188.

Steinman, L. et al. (2006). How to successfully apply animal studies in experimental allergic encephalomyelitis to research on multiple sclerosis. Annals of neurology, 60(1), 12-21.

Streetz, K. et al. (2000). Tumor necrosis factor a in the pathogenesis of human and murine fulminant hepatic failure. Gastroenterology, 119(2), 446-460.

Tee, A. R. et al. (2002). Tuberous sclerosis complex-1 and-2 gene products function together to inhibit mammalian target of rapamycin (mTOR)-mediated downstream signaling. Proceedings of the National Academy of Sciences, 99(21), 13571-13576.

Tee, A. R. et al. (2003). Tuberous sclerosis complex gene products, Tuberin and Hamartin, control mTOR signaling by acting as a GTPase-activating protein complex toward Rheb. Current biology, 13(15), 1259-1268.

Ulich, T. R. et al. (1994). Intratracheal injection of LPS and cytokines. V. LPS induces expression of LIF and LIF inhibits acute inflammation. American Journal of Physiology-Lung Cellular and Molecular Physiology, 267(4), L442-L446.

Van Acker, G. J. et al. (2007). Cause-effect relationships between zymogen activation and other early events in secretagogue-induced acute pancreatitis. American Journal of Physiology-Gastrointestinal and Liver Physiology, 292(6), G1738-G1746.

Van Dartel, S. A. et al. (2013). Predictors for the 5-year risk of serious infections in patients with rheumatoid arthritis treated with anti-tumour necrosis factor therapy: a cohort study in the Dutch Rheumatoid Arthritis Monitoring (DREAM) registry. Rheumatology, 52(6), 1052-1057.

Van Deventer, S. J. (1997). Tumour necrosis factor and Crohn's disease. Gut, 40(4), 443.

Watters, J. J. et al. (2002). A differential role for the mitogen-activated protein kinases in lipopolysaccharide signaling: the MEK/ERK pathway is not essential for nitric oxide and interleukin 1β production. Journal of Biological Chemistry, 277(11), 9077-9087.

Wittig, G. et al. (1958). Benzo-cycloheptatrien, Benzo-cyclooctatrien und Benzo-cyclooctatetraen: VI. Mitteilung über neuartige Synthesen von Cyclopolyenen. Justus Liebigs Annalen der Chemie, 619(1), 10-27.

Yanovsky, I. et al. (2012). Carbamate derivatives of indolines as cholinesterase inhibitors and antioxidants for the treatment of Alzheimer's disease. Journal of medicinal chemistry, 55(23), 10700-10715.

Yao, C. H. et al. (2011). Discovery of novel N-β-d-xylosylindole derivatives as sodium-dependent glucose cotransporter 2 (SGLT2) inhibitors for the management of hyperglycemia in diabetes. Journal of medicinal chemistry, 54(1), 166-178.

Yasuno, F. et al. (2012). Increased binding of peripheral benzodiazepine receptor in mild cognitive impairment-dementia converters measured by positron emission tomography with [11C] DAA1106. Psychiatry Research: Neuroimaging, 203(1), 67-74.

Yeom, C. E. et al. (2007). 1, 8-Diazabicyclo [5.4. 0] undec-7-ene (DBU)-promoted efficient and versatile aza-Michael addition. Tetrahedron, 63(4), 904-909.

Zeeli, S. et al. (2018). Synthesis and biological evaluation of derivatives of indoline as highly potent antioxidant and anti-inflammatory agents. Journal of medicinal chemistry, 61(9), 4004-4019.

* cited by examiner

Brain IL-6

Liver IL-6

Plasma TNF-α

Plasma IL-6

Brain TNF-α

Brain IL-1β

Brain IL-12b

Dose (μmoles of base/kg)

LPS (10 mg/kg)

□ Control
■ Untreated RERT/TSC1 mice
▨ AN-1284 (1 mg/kg)

Figure 10

INDOLINE DERIVATIVES, COMPOSITIONS COMPRISING THEM AND USES THEREOF

CROSS-REFERENCE TO RELATED APPLICATIONS

This application is a National Phase Application of PCT International Application No. PCT/IL2017/050079, International Filing Date Jan. 19, 2017, claiming priority of U.S. Provisional Patent Application No. 62/281,313, filed Jan. 21, 2016, which are hereby incorporated by reference.

TECHNOLOGICAL FIELD

This invention relates to indoline derivatives and salts thereof, compositions comprising them and uses thereof for the treatment of diseases and disorders.

BACKGROUND ART

References considered that are relevant as background to the presently disclosed subject matter are listed below:

Adler S, Kolev M, Varisco P A, Tham M, von Gunten M, Tappeiner C et al. (2013). Induction of severe systemic lupus erythematosus by TNF blockade and response to anti-IL-6 strategy. J Allergy Clin Immunol 131: 1235-1237, 1237 e1231.

Allez M, Karmiris K, Louis E, Van Assche G, Ben-Horin S, Klein A, et al. (2010) Report of the ECCO pathogenesis workshop on anti-TNF therapy failures in inflammatory bowel diseases: definitions, frequency and pharmacological aspects. J Crohns Colitis 4(4):355-366.

Amundsen L H, Nelson L S. (1951). Reduction of nitriles to primary amines with lithium aluminum hydride. J Am Chem Soc 73: 242-244.

Astil B, Boekelheide V. (1958). Synthesis of 5-Ketoliloli-dine. J Org Chem 23: 316-318.

Baumann H, Gauldie J. (1994). The acute phase response. Immunol Today 15: 74-80.

Ben-Horin S, Chowers Y. (2014). Tailoring anti-TNF therapy in IBD: drug levels and disease activity. Nat Rev Gastroenterol Hepatol.11(4):243-255.

Berney T, Gasche Y, Robert J, Jenny A, Mensi N, Grau G, Vermeulen B, and Morel P (1999). Serum profiles of interleukin-6, interleukin-8, and interleukin-10 in patients with severe and mild acute pancreatitis. Pancreas 18:371-377

Bongartz T, Sutton A J, Sweeting M J, Buchan I, Matteson E L, Montori V. (2006). Anti-TNF antibody therapy in rheumatoid arthritis and the risk of serious infections and malignancies: systematic review and meta-analysis of rare harmful effects in randomized controlled trials. JAMA 295: 2275-2285.

Cornu M, Albert V, Hall M N. (2013). mTOR in aging, metabolism, and cancer, Curr Op Gen Dev 23:53-62.

DeFuria J, Belkina A C, Jagannathan-Bogdan M, Snyder-Cappione J, Carr J D, Nersesova Y R et al. (2013). B cells promote inflammation in obesity and type 2 diabetes through regulation of T-cell function and an inflammatory cytokine profile. Proc Natl Acad Sci USA 110: 5133-5138.

DellaGioia N, Devine L, Pittman B, Hannestad J. (2013). Bupropion pre-treatment of endotoxin-induced depressive symptoms. Brain Behav Immun 31: 197-204.

Dhir A, Kulkarni S K. (2007). Involvement of L-arginine-nitric oxide-cyclic guanosine monophosphate pathway in the antidepressant-like effect of venlafaxine in mice. Prog Neuropsychopharmacol Biol Psychiatry 31: 921-925.

Dias V, Junn E, Mouradian M M. (2013). The role of oxidative stress in Parkinson's disease. J Parkinson's Dis 3: 461-491.

Dinarello C A. (1997). Pro-inflammatory and anti-inflammatory cytokines as mediators in the pathogenesis of septic shock. Chest 112: 321S-329S.

Gonzalez-Juanatey C, Vazquez-Rodriguez T R, Miranda-Filloy J A, Gomez-Acebo I, Testa A, Garcia-Porrua C et al. (2012). Anti-TNF-alpha-adalimumab therapy is associated with persistent improvement of endothelial function without progression of carotid intima-media wall thickness in patients with rheumatoid arthritis refractory to conventional therapy. Mediators Inflamm 2012: 674265.

Hajjar D P, Gotto A M, Jr. (2013). Biological relevance of inflammation and oxidative stress in the pathogenesis of arterial diseases. Am J Pathol 182: 1474-1481.

Irony-Tur-Sinai M, Grigoriadis N, Lourbopoulos A, Pinto-Maaravi F, Abramsky O, Brenner T. (2006). Amelioration of autoimmune neuroinflammation by recombinant human alpha-fetoprotein. Exp Neurol 198: 136-144.

Kanasaki K, Taduri G, Koya D. (2013). Diabetic nephropathy: the role of inflammation in fibroblast activation and kidney fibrosis. Front Endocrinol (Lausanne). February 6; 4: 7-15.

Levitt J E, Matthay M A. (2006). Treatment of acute lung injury: historical perspective and potential future therapies. Semin Respir Crit Care Med 27: 426-437.

Maes M. (1999). Major depression and activation of the inflammatory response system. Adv Exp Med Biol 461: 25-46.

Maes M. (2013). Inflammatory and oxidative and nitrosative stress cascades as new drug targets in myalgic encephalomyelitis and chronic fatigue syndrome. Mod Trends Pharmacopsychiatry 28: 162-174.

Magro F, Portela F. (2010). Management of inflammatory bowel disease with infliximab and other anti-tumor necrosis factor alpha therapies. BioDrugs 24 Suppl 1: 3-14.

Mandell B F, Sobell J M. (2014). The role of TNF inhibitors in psoriatic disease. Semin Cutan Med Surg 33: S64-68.

Mangialasche F, Polidori M C, Monastero R, Ercolani S, Camarda C, Cecchetti R et al. (2009). Biomarkers of oxidative and nitrosative damage in Alzheimer's disease and mild cognitive impairment. Ageing Res Rev 8: 285-305.

Martinez-Castelao A, Navarro-Gonzalez J F, Gorriz J L, de Alvaro F (2015). The Concept and the Epidemiology of Diabetic Nephropathy Have Changed in Recent Years. J Clin Med 4:1207-1216

McInnes I B, Schett G. (2007). Cytokines in the pathogenesis of rheumatoid arthritis. Nat Rev Immunol 7: 429-442.

Muyderman H, Chen T. (2014). Mitochondrial dysfunction in amyotrophic lateral sclerosis—a valid pharmacological target? Br J Pharmacol 171: 2191-2205.

Nakamura Y, Ohta T, Oe Y. (2015). A formal anti-Markovnikov hydroamination of allylic alcohols via tandem oxidation/1,4-conjugate addition/1,2-reduction using a Ru catalyst. Chem Commun 51: 7459-7462.

Naziroglu M, Dikici D M, Dursun S. (2012). Role of oxidative stress and Ca(2)(+) signaling on molecular pathways of neuropathic pain in diabetes: focus on TRP channels. Neurochem Res 37: 2065-2075.

Nickoloff B J, Qin J Z, Nestle F O. (2007). Immunopathogenesis of psoriasis. Clin Rev Allergy Immunol 33: 45-56.

3

Norman J (1998). The role of cytokines in the pathogenesis of acute pancreatitis. Am J Surg 175:76-83.

Olsson B, Hertze J, Lautner R, Zetterberg H, Nagga K, Hoglund K et al. (2013). Microglial markers are elevated in the prodromal phase of Alzheimer's disease and vascular dementia. J Alzheimers Dis 33: 45-53.

Overwater I E, Bindels-de Heus K, Rietman A B, Ten Hoopen L W, Vergouwe Y, Moll H A, de Wit M C. (2015) Epilepsy in children with tuberous sclerosis complex: Chance of remission and response to antiepileptic drugs, Epilepsia, 56:1239-1245.

Paracatu L C, Bonacorsi C, de Farias C M, Nazare A C, Petronio M S, Regasini L O et al. (2014). Alkyl caffeates as anti-Helicobacter pylori and scavenger of oxidants produced by neutrophils. Med Chem 10: 74-80.

Petrovna, V T, Vladimirovna V D, Nikolaevich O S. (2010). Method for synthesis of 1-(aminoalkyl)indolines. Patent RU 2387640.

Podolsky D K. (2002). Inflammatory bowel disease. N Engl J Med 347: 417-429. Pradhan S, Andreasson K. (2013). Commentary: Progressive inflammation as a contributing factor to early development of Parkinson's disease. Exp Neurol 241: 148-155.

Raaschou P, Simard J F, Holmqvist M, Askling J, Group A S. (2013). Rheumatoid arthritis, anti-tumour necrosis factor therapy, and risk of malignant melanoma: nationwide population based prospective cohort study from Sweden. BMJ 346: f1939.

Reichert F, Rotshenker S. (2003). Complement-receptor-3 and scavenger-receptor-AI/II mediated myelin phagocytosis in microglia and macrophages. Neurobiol Dis 12: 65-72.

Reuter S, Gupta S C, Chaturvedi M M, Aggarwal B B. (2010). Oxidative stress, inflammation, and cancer: how are they linked? Free Radic Biol Med 49: 1603-1616.

Rodrigo R, Fernandez-Gajardo R, Gutierrez R, Matamala J M, Carrasco R, Miranda-Merchak A et al. (2013). Oxidative stress and pathophysiology of ischemic stroke: novel therapeutic opportunities. CNS Neurol Disord Drug Targets 12: 698-714.

Rongioletti F, Burlando M, Parodi A. (2014) Inflammatory/infectious cutaneous side effects of biological drugs in patients with psoriasis: a general review with personal data. G Ital Dermatol Venereol 149: 311-316.

Roy S, Eastman A, Gribble G W. (2005). Synthesis of 7-keto-Go6976 (ICP-103). Synth Commun, 35: 595-601.

Roy S, Eastman A, Gribble G W. (2006). Synthesis of N-alkyl substituted bioactive indolocarbazoles related to Go6976. Tetrahedron, 62: 7838-7845.

Rubino M T, Maggi D, Laghezza A, Loiodice F, Tortorella P. (2011). Identification of novel matrix metalloproteinase inhibitors by screening of phenol fragments library. Arch Pharm Chem.Life Sci. 344: 557-563

Schrag M, Mueller C, Zabel M, Crofton A, Kirsch W M, Ghribi O et al. (2013). Oxidative stress in blood in Alzheimer's disease and mild cognitive impairment: a meta-analysis. Neurobiol Dis 59: 100-110.

Schmid R M and Adler G (1999). Cytokines in acute pancreatitis: New pathophysiological concepts evolve. Eur J Gastroenterol Hepatol 125-127.

Schulz E, Anter E, Keaney J F, Jr. (2004). Oxidative stress, antioxidants, and endothelial function. Curr Med Chem 11: 1093-1104.

Seror R, Richez C, Sordet C, Rist S, Gossec L, Direz G et al. (2013). Pattern of demyelination occurring during anti-TNF-alpha therapy: a French national survey. Rheumatology (Oxford) 52: 868-874.

4

Shapiro S L, Rose I M, Freedman L. (1959). Aminoalkyl-amides and Oxazolidinediones. J Am Chem Soc 81: 3083-3088.

Shirota O, Hakamata W, Goda Y. (2003) Concise large-scale synthesis of psilocin and psilocybin, principal hallucinogenic constituents of "magic mushroom". J Nat Prod 66: 885-887.

Smith K J, Kapoor R, Felts P A. (1999). Demyelination: the role of reactive oxygen and nitrogen species. Brain Pathol 9: 69-92.

Smith M A, Nunomura A, Lee H G, Zhu X, Moreira P I, Avila J et al. (2005). Chronological primacy of oxidative stress in Alzheimer disease. Neurobiol Aging 26: 579-580.

Song C, Halbreich U, Han C, Leonard B E, Luo H. (2009). Imbalance between pro- and anti-inflammatory cytokines, and between Th1 and Th2 cytokines in depressed patients: the effect of electroacupuncture or fluoxetine treatment. Pharmacopsychiatry 42: 182-188.

Steinman L, Zamvil S S. (2006). How to successfully apply animal studies in experimental allergic encephalomyelitis to research on multiple sclerosis. Ann Neurol 60: 12-21.

Streetz K, Leifeld L (2000). Grundmann D, Ramakers J, Eckert K, Spengler U, et al. Tumor necrosis factor alpha in the pathogenesis of human and murine fulminant hepatic failure. Gastroenterology 119:446-460.

Su K H, Cuthbertson C. Christophi C. (2006) Review of experimental animal models of acute pancreatitis. HPB. 8:264-286.

Tee A R, Fingar D C, Manning B D, Kwiatkowski D J, Cantley L C, Blenis J: (2002). Tuberous sclerosis complex-1 and -2 gene products function together to inhibit mammalian target of rapamycin (mTOR)-mediated downstream signaling, Proc Natl Acad Sci USA, 99:13571-13576.

Tee A R, Manning B D, Roux P P, Cantley L C, Blenis J. (2003). Tuberous sclerosis complex gene products, Tuberin and Hamartin, control mTOR signaling by acting as a GTPase-activating protein complex toward Rheb, Current Biol 13:1259-1268.

Ulich T R, Fann M J, Patterson P H, Williams J H, Samal B, Del Castillo J et al. (1994). Intratracheal injection of LPS and cytokines. V. LPS induces expression of LIF and LIF inhibits acute inflammation. Am J Physiol 267: L442-446.

Undine E. Borgwardt L. S. (2013) Molecular Mechanisms of Depression: Perspectives on New Treatment Strategies Cell Physiol Biochem 31:761-777.

Van Acker G J D, Weiss E, Steer M L. Perides G. (2007). Cause-effect relationships between zymogen activation and other early events in secretagogue-induced acute pancreatitis. Am. J. Physiol. Gastrointes. Liver Physiol; 292: G1738-G1746.

van Dartel S A, Fransen J, Kievit W, Dutmer E A, Brus H L, Houtman N M et al. (2013). Predictors for the 5-year risk of serious infections in patients with rheumatoid arthritis treated with anti-tumour necrosis factor therapy: a cohort study in the Dutch Rheumatoid Arthritis Monitoring (DREAM) registry. Rheumatology (Oxford) 52: 1052-1057.

Van Deventer S J. (1997). Tumour necrosis factor and Crohn's disease. Gut 40: 443-448.

Watters J J, Sommer J A, Pfeiffer Z A, Prabhu U, Guerra A N, Bertics R I (2002). A differential role for the mitogen-activated protein kinases in lipopolysaccharide signaling: the MEK/ERK pathway is not essential for nitric oxide and interleukin lbeta production. J Biol Chem 277: 9077-9087.

5

Wittig G, Eggers H, Duffner P. (1958). Benzo-cyclohep-
tatrien, Benzo-cyclooctatrien and Benzo-cyclooctatet-
raen: VI. Mitteilung über neuartige Synthesen von
Cyclopolyenen. Justus Liebigs Ann Chem. 619: 10-27

Yanovsky I, Finkin-Groner E, Zaikin A, Lerman L, Shalom
H, Zeeli S, Weill T, Ginsburg I, Nudelman A, Weinstock
M. (2012) Carbamate Derivatives of Indolines as Cholin-
esterase Inhibitors and Antioxidants for the Treatment of
Alzheimer's Disease. J Med Chem 55: 10700-10715.

Yao C-H, Song J-S, Chen C-T, Yeh T-K, Hung M-S, Chang,
C-C, Liu, Y-W, Yuan, M-C, Hsieh, C-J, Huang, C-Y,
Wang, M-H, Chiu, C-H, Hsieh, T-C, Wu, S-H, Hsiao,
W-C, Chu, K-F, Tsai, C-H, Chao, Y-S, Lee, J-C, et al.
(2010). Discovery of novel N-β-d-xylosylindole deriva-
tives as sodium-dependent glucose cotransporter 2
(SGLT2) inhibitors for the management of hyperglycemia
in diabetes. J Med Chem, 54: 166-178

Yasuno F, Kosaka J, Ota M, Higuchi M, Ito H, Fujimura Y
et al. (2012). Increased binding of peripheral benzodiaz-
epine receptor in mild cognitive impairment-dementia
converters measured by positron emission tomography
with [(1)(1)C]DAA1106. Psychiatry Res 203: 67-74.

Yeom C-E, Kim M J, Kim B M. (2007). 1,8-Diazabicyclo
[5.4.0]undec-7-ene (DBU)-promoted efficient and versa-
tile aza-Michael addition. Tetrahedron, 63: 904-909

Acknowledgement of the above references herein is not to
be inferred as meaning that these are in any way relevant to
the patentability of the presently disclosed subject matter.

BACKGROUND

Inflammation is a normal response to infection and injury
and involves the recruitment of immune systems to neutral-
ize invading pathogens, repair injured tissues and promote
wound healing. (Baumann and Gauldie, 1994). Inflamma-
tion is a normal response to infection and injury and involves
the recruitment of immune systems to neutralize invading
pathogens, repair injured tissues and promote wound heal-
ing. (Baumann and Gauldie, 1994). However, chronic or
excessive activation of the immune system is associated
with an increase in reactive oxygen species (ROS) (Watters
et al., 2002), prolonged activation of inducible nitric oxide
synthase (iNOS) and the release of pro-inflammatory cyto-
kines e.g. tumor necrosis factor-α (TNF-α), interleukin 6
(IL-6), interleukin 1β (IL-1β) (Watters et al., 2002), all of
which may increase susceptibility to infections. ROS and
pro-inflammatory cytokines have been implicated in a vari-
ety of disorders. They include, septic shock (Dinarello,
1997), acute respiratory distress syndrome (Levitt and Mat-
thay, 2006), which can be caused by gram-negative bacteria
(Ulich et al., 1994), demyelinating disorders, multiple scle-
rosis and Guillain-Barré syndrome (Smith et al., 1999),
ulcerative colitis (Podolsky, 2002), Crohn's disease (Van
Deventer, 1997), rheumatoid arthritis (McInnes and Schett,
2007), diabetes, (DeFuria et al., 2013) and diabetic neph-
ropathy (Kanasaki et al., 2013), atherosclerosis (Hajjar and
Gotto, 2013), acute liver failure (Streetz et al, 2000), chronic
fatigue syndrome (Maes 2013) neuropathic pain (Nazıroğlu
et al., 2012), psoriasis (Nickoloff et al., 2007) and cancer
(Reuter et al., 2010)

Drugs that block the action of TNF-α have proved to be
very effective in the treatment of ulcerative colitis, rheuma-
toid arthritis (Magro and Portela, 2010; Gonzalez-Juanatey
et al., 2012; Sorrentino, 2013) and psoriasis (Mandell and
Sobell, 2014). However, their chronic use may increase the
risk of serious adverse effects, (Raaschou et al., 2013;
Bongartz et al., 2006; van Dartel et al., 2013; Seror et al., 2013; Adler et al., 2013; Rongioletti et al., 2014). Also,
approximately 33% of patients either do not respond to them
or lose response over time within the first 12 months of
therapy (Ben Horin et al., 2011), possibly because of the
presence of neutralizing antibodies raised against the bio-
logical drug. TNF-α antagonists may also cause allergic
reactions like myalgias and arthralgias and increase the
incidence of infections and lymphomas (Allez et al., 2010).

Impaired mitochondrial function, the production of ROS
and an increase in pro-inflammatory cytokines play a key
role in the aetiology of Alzheimer's disease (AD) (Man-
gialasche et al., 2009). These pathological changes are also
seen in Mild Cognitive Impairment, a prodromal form of AD
(Schrag et al., 2013; Olsson et al., 2013; Yasuno et al., 2013),
to which it progresses in a significant proportion of subjects.
Oxidative stress and pro-inflammatory cytokines may con-
tribute to neurodegeneration in other disorders, such as
Parkinson's disease (Dias et al., 2013; Pradhan et al., 2013),
ischemic stroke (Rodrigo et al., 2013) and amyotrophic
lateral sclerosis (Muyderman et al., 2014), and depression
(Undine and Borgwardt (2013). An increase in the activation
of iNOS and in the levels of pro-inflammatory cytokines has
also been implicated in major depressive disorder (Maes
1999; Song et al., 2009) and may be restored to normal by
treatment with antidepressants (Dhir and Kulkarni 2007;
DellaGioia et al., 2013). For all these conditions there is
therefore a need for therapeutic agents that can reduce the
damaging effect of oxidative stress and the excessive release
of NO and pro-inflammatory cytokines without blocking
their receptors, so as not to prevent potentially beneficial
effects of the cytokines in other tissues.

Tuberous sclerosis (TS) is a highly prevalent autosomal
recessive genetic disease that occurs in approximately
1:6000 births. It causes multi-organ pathologies primarily in
the central nervous system (CNS), and in the form of
non-malignant tumours, referred to as hamartomas. The
CNS defects of TS patients are manifested in epileptic
seizures, developmental delays, intellectual disability and
autism. The disease, referred to as tuberous sclerosis com-
plex (TSC), has a wide spectrum of severity, which can vary
widely between individuals, even between identical twins.
This implicates factors other than the genetic lesions them-
selves as critical for the propagation of the disease. Two
genes have been identified as the cause of TSC, hamartin
(a.k.a. TSC1) located on chromosome 9 and tuberin (a.k.a.
TSC2) located on chromosome 16. A lesion in one of these
genes is sufficient to confer the disease. In 2002, TSC was
found to function as a key negative regulator of the mam-
malian target of rapamycin (mTOR), a serine threonine
kinase that controls cell metabolism (Tee et al., 2002).
Mechanistically, TSC1 and TSC2 form a heterodimer to
activate the GTPase activity of Rheb, a G-protein critical for
the assembly of mTOR into an active complex (Tee et al.,
2003). In the absence of either TSC1 or TSC2, mTOR is
hyperactive. Because mTOR suppression leads to cessation
of growth, the gain-of-function mutations in the signalling
elements that control mTOR are found in the majority of
tumours to support their growth under suboptimal condi-
tions (Cornu et al., 2013). Since TSC patients have an
exaggerated mTOR activity the obvious pharmacological
strategy for treatment is the use of mTOR inhibitors, such as
rapamycin. Rapamycin does not bind mTOR directly, rather
inhibits FKBP12, a peptidyl-prolyl cis-trans isomerase nec-
essary for the assembly of mTORC1. In the presence of
rapamycin mTORC1 disassembles quickly. The disassembly
of mTORC2 requires higher concentrations and a longer
exposure time. Rapamycin is used as an immunosuppressant following organ transplantation to prevent acute rejection and in graft versus host disease. Everolimus an analogue of rapamycin with better pharmacokinetic properties has been approved by the FDA for the treatment of adults with non-surgically removable brain tumours called subependymal giant cell astrocytomas (SEGA) associated with TSC. This indication was later extended to children.

A second major complication of TSC is the development of kidney tumours called renal angiomyolipomas, which have been reported in up to 75% of patients with the genetic disorder TSC. Lesions are usually multiple, bilateral, and progressive. Other complications of TSC are lung cysts termed lymphangioleiomyomatosis (LAM), a progressive lung disease that usually strikes women during their child-bearing years. mTOR inhibitors have some clinical benefit in this condition but do not fully prevent disease progression.

The most prevalent symptom of TSC are epileptic seizures, seen from the first year of life, caused by the abnormalities of neuronal migration, cellular differentiation and excessive cellular proliferation. Seizures have a focal or multifocal origin, are often resistant to antiepileptic drugs and impede neurocognitive development. Vigabatrin has proved to be effective against infantile spasms due to TSC (Overwater et al., 2010) but has many side effects in the CNS and periphery and is teratogenic. The genotype-phenotype correlation in TSC is weak so that specific mutations can have a large spectrum of clinical severities, suggesting the influence of other factors on disease progression. This may include the immune system. The molecules of the present application have a broad range of activities, showing no signs of toxicity (in healthy mice), even at a several-fold higher dose, which enable them to be general immunomodulators for various inflammatory conditions.

Diabetic nephropathy (DN) is the most common complication and leading cause of mortality associated with diabetes (Martinez et al., 2015) and its occurrence is expected to increase with diabetes prevalence. Numerous factors, both environmental and genetic, influence the onset, severity and the rate of progression of DN. DN begins with glomerular and tubular hypertrophy and the thickening of the basement membrane and expansion of the mesangium leading to end-stage glomerular closure and tubulointerstitial fibrosis. Inflammation plays a critical role in the pathogenesis, development and progression of diabetic nephropathy (Kanasaki et al., 2013).

The severity of pancreatitis results from immunologic events subsequent to acinar cell injury, including the activation and recruitment of inflammatory cells, the local and systemic production and/or release of cytokines, and the final transmigration of those activated inflammatory cells across the endothelial barrier into the involved tissue (Berney et al., 1999). Experimental evidence therefore suggests that up-regulation of inflammatory mediators including cytokines, chemokines, adhesion molecules, and inducible nitric oxide has a central role in this pathologic process (Norman, 1998; Schmid and Adler, 1999). In humans and experimental animals, the severity of pancreatitis is characterised by elevation in serum amylase

GENERAL DESCRIPTION

The present invention provides a compound of general formula (I), including any stereoisomer and salt thereof:

(I)

wherein $R_1$ is selected from $C_1$-$C_{10}$ alkoxy, aryloxy, benzyloxy, hydroxy, halogen, straight or branched $C_1$-$C_5$ alkyl, straight or branched $C_2$-$C_6$ alkenyl; straight or branched $C_2$-$C_6$ alkynyl;

$R_2$ is selected from straight or branched $C_2$-$C_8$ alkyl, straight or branched $C_2$-$C_8$ alkenyl; straight or branched $C_2$-$C_8$ alkynyl; wherein said alkyl, alkenyl and alkynyl are each substituted by at least one group selected from —OH, —C(=O)O($C_1$-$C_5$alkyl), —C(=O)OH, and —C(=O)$NR_3R_4$;

$R_3$ and $R_4$ are each independently selected from H, straight or branched $C_1$-$C_{10}$ alkyl and aryl.

In another aspect the invention provides a compound of general formula (I), including any stereoisomer and salt thereof:

(I')

wherein $R_1$ is selected from $C_1$-$C_{10}$ alkoxy, aryloxy, benzyloxy, hydroxy, halogen, straight or branched $C_1$-$C_5$ alkyl, straight or branched $C_2$-$C_6$ alkenyl; straight or branched $C_2$-$C_6$ alkynyl;

$R_2$ is selected from straight or branched $C_2$-$C_8$ alkyl, straight or branched $C_2$-$C_8$ alkenyl; straight or branched $C_2$-$C_8$ alkynyl; wherein said alkyl, alkenyl and alkynyl are each substituted by at least one of —$NH_2$, —$NHR_5$, —$NR_6R_7$;

$R_5$, $R_6$, and $R_7$ are each independently selected from straight or branched $C_1$-$C_{10}$ alkyl and aryl;

provided that when $R_2$ is $C_2$ alkyl it is substituted by at least one of —$NHR_5$, —$NR_6R_7$; and provided that when $R_2$ is a straight $C_3$-$C_8$ alkyl it is substituted by at least one of —$NH_2$, —$NHR_5$ and —$NR_6R_7$ wherein $R_5$, $R_6$, and $R_7$ are each independently selected from branched $C_3$-$C_{10}$ alkyl or an aryl.

In some embodiments, $R_1$ is selected from $C_1$-$C_{10}$ alkoxy, aryloxy, benzyloxy, hydroxy and halogen. In other embodiments, $R_1$ is —O($C_1$-$C_5$ alkyl). In further embodiments, $R_1$ is a halogen. In other embodiments, $R_1$ is benzyloxy. In other embodiments $R_1$ is a hydroxy.

In yet further embodiments, $R_1$ is substituted at position 4. In other embodiments, $R_1$ is substituted at position 5. In further embodiments, $R_1$ is substituted at position 6. In yet other embodiments, $R_1$ is substituted at position 7.

In some embodiments, $R_2$ is a straight or branched $C_2$-$C_8$ alkyl substituted by at least one group selected from —OH, —C(=O)O($C_1$-$C_5$alkyl), —C(=O)OH and —C(=O)$NR_3R_4$. In other embodiments, $R_2$ is a straight or branched $C_2$-$C_8$ alkyl substituted by at least one —OH. In yet further embodiments, $R_2$ is a straight or branched $C_2$-$C_8$ alkyl substituted by at least one —C(=O)O($C_1$-$C_5$alkyl). In other embodiments, $R_2$ is a straight or branched $C_2$-$C_8$ alkyl substituted by at least one —C(=O)NR$_3$R$_4$, wherein $R_3$ and $R_4$ are each independently and differently selected from H, straight or branched $C_1$-$C_{10}$ alkyl and aryl In other embodiments $R_2$ is substituted by at least one of —NH$_2$, —NHR$_5$, —NR$_6$R$_7$. In other embodiments $R_2$ is substituted by at least one —NH$_2$. In further embodiments $R_2$ is substituted by at least one —NHR$_5$. In yet further embodiments $R_2$ is substituted by at least one —NR$_6$R$_7$.

In some embodiments, a compound of the invention is in a form of a pharmaceutically acceptable salt thereof.

In another aspect the invention provides a compound as disclosed herein, for use as a medicament.

In another one of its aspects the present invention provides a pharmaceutical composition comprising a compound of general formula (I), including any stereoisomer and salt thereof:

(I)

wherein $R_1$ is selected from $C_1$-$C_{10}$ alkoxy, aryloxy, benzyloxy, hydroxy, halogen, straight or branched $C_1$-$C_5$ alkyl, straight or branched $C_2$-$C_6$ alkenyl; straight or branched $C_2$-$C_6$ alkynyl;

$R_2$ is selected from straight or branched $C_2$-$C_8$ alkyl, straight or branched $C_2$-$C_8$ alkenyl; straight or branched $C_2$-$C_8$ alkynyl; wherein said alkyl, alkenyl and alkynyl are each substituted by at least one group selected from —OH, —C(=O)O ($C_1$-$C_5$alkyl), —C(=O)OH, —NR$_3$R$_4$ and —C(=O)NR$_5$R$_6$;

$R_3$, $R_4$, $R_5$ and $R_6$ are each independently selected from H, straight or branched $C_1$-$C_{10}$ alkyl and aryl.

In yet another aspect, the invention provides a compound as disclosed herein, for use in immunomodulation of a condition, disease or disorder caused by an immune response.

In yet another aspect, the invention provides a compound as disclosed herein, for use in the reduction of at least one condition selected from oxidative stress, release of NO and release of pro-inflammatory cytokines.

In yet another aspect, the invention provides a compound as disclosed herein, for use in the inhibition of at least one of oxidative stress and inflammation.

In another aspect, the invention provides a compound as disclosed herein for use in the prevention, treatment or slowing the progression of a neurodegenerative disease, disorder or condition including any symptoms thereof.

In yet another aspect, the invention provides a compound as disclosed herein for use in the prevention, treatment or slowing the progression of an inflammatory disease, disorder or condition including any symptoms thereof.

In a further aspect, the invention provides a compound as disclosed herein, for use in the treatment, prevention or slowing the progression of a disease, disorder, condition or symptom selected from at least one of Alzheimer's disease, Parkinson's disease, depression, ischemic stroke, amyotrophic lateral sclerosis, multiple sclerosis, mild cognitive impairment, ulcerative colitis, Crohn's disease, pancreatitis, rheumatoid arthritis, diabetes, cardiac failure, chronic liver disease, chronic lung disease, meningitis, infective brain disease, complex regional pain syndrome (CRPS), tuberous sclerosis, psoriasis, and any combinations thereof.

In a further aspect, the invention provides a compound as disclosed herein, for use in the treatment, prevention or slowing the progression of pancreatitis.

In another one of its aspects, the invention provides a composition comprising a compound as disclosed herein.

In another aspect, the invention provides the use of a compound as disclosed herein, for the preparation of a medicament.

In yet another aspect, the invention provides use of a compound as disclosed herein, for the preparation of an immunomodulator for the treatment of a condition, disease or disorder caused by an immune response.

In another aspect, the invention provides the use of a compound as disclosed herein, for the preparation of a medicament for the treatment of a disease, disorder, condition or symptom associated with the inhibition of at least one of oxidative stress and inflammation.

In another aspect, the invention provides the use of a compound as disclosed herein, for the preparation of a medicament for the reduction of at least one condition selected from oxidative stress, release of NO and release of pro-inflammatory cytokines.

In some embodiments, said disease, disorder, condition or symptom is selected from at least one of the following; Alzheimer's disease, Parkinson's disease, depression, ischemic stroke, amyotrophic lateral sclerosis, multiple sclerosis, mild cognitive impairment, ulcerative colitis, Crohn's disease, pancreatitis, rheumatoid arthritis, diabetes, cardiac failure, chronic and acute liver disease, chronic lung disease, meningitis, infective brain disease, complex regional pain syndrome (CRPS), tuberous sclerosis, psoriasis and any combinations thereof.

In another aspect, the invention provides the use a compound of general formula (I″), including any stereoisomer and salt thereof:

(I″)

wherein $R_1$ is selected from H, OH, $C_1$-$C_{10}$ alkoxy, aryloxy, benzyloxy, halogen, straight or branched $C_1$-$C_5$ alkyl, straight or branched $C_2$-$C_6$ alkenyl; straight or branched $C_2$-$C_6$ alkynyl;

$R_2$ is selected from straight or branched $C_2$-$C_8$ alkyl, straight or branched $C_2$-$C_8$ alkenyl; straight or branched $C_2$-$C_8$ alkynyl; wherein said alkyl, alkenyl and alkynyl are each substituted by at least one group selected from —C(=O)O($C_1$-$C_5$alkyl), —C(=O)OH, —C(=O)NR$_3$R$_4$, —NHR$_5$ and —NR$_6$R$_7$;

$R_3$, $R_4$, $R_5$, $R_6$ and $R_7$ are each independently selected from H, straight or branched $C_1$-$C_{10}$ alkyl and aryl;

for the preparation of a medicament for the reduction of at least one condition selected from oxidative stress, release of NO and release of pro-inflammatory cytokine.

In another aspect, the invention provides the use a compound of general formula (I''), including any stereoisomer and salt thereof:

(I'')

wherein $R_1$ is selected from H, OH, $C_1$-$C_{10}$ alkoxy, aryloxy, benzyloxy, halogen, straight or branched $C_1$-$C_5$ alkyl, straight or branched $C_2$-$C_6$ alkenyl; straight or branched $C_2$-$C_6$ alkynyl;

$R_2$ is selected from straight or branched $C_2$-$C_8$ alkyl, straight or branched $C_2$-$C_8$ alkenyl; straight or branched $C_2$-$C_8$ alkynyl; wherein said alkyl, alkenyl and alkynyl are each substituted by at least one group selected from —C(=O)O($C_1$-$C_5$alkyl), —C(=O)OH, —C(=O)NR$_3$R$_4$, —NHR$_5$ and —NR$_6$R$_7$;

$R_3$, $R_4$, $R_5$, $R_6$ and $R_7$ are each independently selected from H, straight or branched $C_1$-$C_{10}$ alkyl and aryl; for the preparation of a medicament for the inhibition of at least one of oxidative stress, inflammation.

In another aspect, the invention provides the use a compound of general formula (I''), including any stereoisomer and salt thereof:

(I'')

wherein $R_1$ is selected from H, OH, $C_1$-$C_{10}$ alkoxy, aryloxy, benzyloxy, halogen, straight or branched $C_1$-$C_5$ alkyl, straight or branched $C_2$-$C_6$ alkenyl; straight or branched $C_2$-$C_6$ alkynyl;

$R_2$ is selected from straight or branched $C_2$-$C_8$ alkyl, straight or branched $C_2$-$C_8$ alkenyl; straight or branched $C_2$-$C_8$ alkynyl; wherein said alkyl, alkenyl and alkynyl are each substituted by at least one group selected from —C(=O)O($C_1$-$C_5$alkyl), —C(=O)OH, —C(=O)NR$_3$R$_4$, —NHR$_5$ and —NR$_6$R$_7$;

$R_3$, $R_4$, $R_5$, $R_6$ and $R_7$ are each independently selected from H, straight or branched $C_1$-$C_{10}$ alkyl and aryl; for the preparation of a medicament for the prevention, treatment or slowing the progression of a neurodegenerative disease, disorder or condition including any symptoms thereof.

In another aspect, the invention provides the use a compound of general formula (I''), including any stereoisomer and salt thereof:

(I'')

wherein $R_1$ is selected from H, OH, $C_1$-$C_{10}$ alkoxy, aryloxy, benzyloxy, halogen, straight or branched $C_1$-$C_5$ alkyl, straight or branched $C_2$-$C_6$ alkenyl; straight or branched $C_2$-$C_6$ alkynyl;

$R_2$ is selected from straight or branched $C_2$-$C_8$ alkyl, straight or branched $C_2$-$C_8$ alkenyl; straight or branched $C_2$-$C_8$ alkynyl; wherein said alkyl, alkenyl and alkynyl are each substituted by at least one group selected from —C(=O)O($C_1$-$C_5$alkyl), —C(=O)OH, —C(=O)NR$_3$R$_4$, —NHR$_5$ and —NR$_6$R$_7$;

$R_3$, $R_4$, $R_5$, $R_6$ and $R_7$ are each independently selected from H, straight or branched $C_1$-$C_{10}$ alkyl and aryl; for the preparation of a medicament for the prevention, treatment or slowing the progression of an inflammatory disease, disorder or condition including any symptoms thereof.

In another aspect, the invention provides the use a compound of general formula (I''), including any stereoisomer and salt thereof:

(I'')

wherein $R_1$ is selected from H, OH, $C_1$-$C_{10}$ alkoxy, aryloxy, benzyloxy, halogen, straight or branched $C_1$-$C_5$ alkyl, straight or branched $C_2$-$C_6$ alkenyl; straight or branched $C_2$-$C_6$ alkynyl;

$R_2$ is selected from straight or branched $C_2$-$C_8$ alkyl, straight or branched $C_2$-$C_8$ alkenyl; straight or branched $C_2$-$C_8$ alkynyl; wherein said alkyl, alkenyl and alkynyl are each substituted by at least one group selected from —C(=O)O($C_1$-$C_5$alkyl), —C(=O)OH, —C(=O)NR$_3$R$_4$, —NHR$_5$ and —NR$_6$R$_7$;

$R_3$, $R_4$, $R_5$, $R_6$ and $R_7$ are each independently selected from H, straight or branched $C_1$-$C_{10}$ alkyl and aryl; for the preparation of a medicament for immunomodulation of a condition, disorder or disease associated with an immune response.

The invention further provides a pharmaceutical composition comprising a compound of general formula (II), including any stereoisomer and salt thereof:

(II)

wherein

R$_2$ is selected from straight or branched C$_2$-C$_8$ alkyl, straight or branched C$_2$-C$_8$ alkenyl; straight or branched C$_2$-C$_8$ alkynyl; wherein said alkyl, alkenyl and alkynyl are each substituted by at least one group selected from —C(═O)O(C$_1$-C$_5$alkyl), —C(═O) NR$_3$R$_4$, —NHR$_5$ and —NR$_6$R$_7$;

R$_3$, R$_4$, R$_5$, R$_6$ and R$_7$ are each independently selected from H, straight or branched C$_1$-C$_{10}$ alkyl and aryl wherein R$_5$ is different than H; and at least one of R$_3$ and R$_4$ or at least one of R$_6$ and R$_7$ is different than H.

In some embodiments of the above aspect, R$_2$ is a straight or branched C$_2$-C$_8$ alkyl substituted by at least one group selected from —C(═O)NR$_3$R$_4$, —NHR$_5$ and —NR$_6$R$_7$; R$_3$, R$_4$, R$_5$, R$_6$ and R$_7$ are each independently selected from H, straight or branched C$_1$-C$_{10}$ alkyl wherein R$_5$ is different than H and at least one of R$_3$ and R$_4$ or at least one of R$_6$ and R$_7$ is different than H.

In further embodiments of the above aspect, R$_2$ is a straight or branched C$_2$-C$_8$ alkyl substituted by at least one —NHR$_5$ or —NR$_6$R$_7$; wherein R$_5$, R$_6$, and R$_7$ are each independently selected from H, straight or branched C$_1$-C$_{10}$ alkyl, and wherein R$_5$ is different than H and at least one of R$_3$ and R$_4$ is different than H.

In other embodiments of the above aspect, R$_2$ is a straight or branched C$_2$-C$_8$ alkyl substituted by at least one —C(═O)NR$_3$R$_4$; wherein R$_3$ and R$_4$ are each independently selected from H, straight or branched C$_1$-C$_{10}$ alkyl and wherein at least one of R$_3$ and R$_4$ is different than H.

In some embodiments of the above aspect, a compound of formula (II) is:

The invention further provides a use of a compound of general formula (II'), including any stereoisomer and salt thereof:

(II')

wherein

R$_2$ is selected from straight or branched C$_2$-C$_8$ alkyl, straight or branched C$_2$-C$_8$ alkenyl; straight or branched C$_2$-C$_8$ alkynyl; wherein said alkyl, alkenyl and alkynyl are each substituted by at least one group selected from —OH, —C(═O)O(C$_1$-C$_5$alkyl), —C(═O)OH, —C(═O)NR$_3$R$_4$, —NHR$_5$ and —NR$_6$R$_7$;

R$_3$, R$_4$, R$_5$ R$_6$ and R$_7$ are each independently selected from H, straight or branched C$_1$-C$_{10}$ alkyl and aryl;

for the preparation of a medicament for the prevention, treatment or slowing the progression of a disease, disorder or condition including any symptoms thereof, selected from inflammatory disease, neurodegenerative disease, disease associated with at least one of oxidative stress, an immune response, release of NO and release of pro-inflammatory cytokine.

In some embodiments of the above aspect, R$_2$ is a straight or branched C$_2$-C$_8$ alkyl substituted with —C(═O)NR$_3$R$_4$, —NHR$_5$ and —NR$_6$R$_7$. In some further embodiments R$_2$ is substituted with —NR$_3$R$_4$. In other embodiments R$_2$ is substituted with —NHR$_5$ and —NR$_6$R$_7$. In other embodiments R$_2$ is substituted with —C(═O)NR$_3$R$_4$. In other embodiments, R$_2$ is substituted with OH. In further embodiments, R$_2$ is substituted with —C(═O)O(C$_1$-C$_5$alkyl).

In some embodiments of the above aspect, a compound of formula (II) is selected from:

In a further aspect the invention provides a pharmaceutical composition comprising a compound of general formula (III), including any stereoisomer and salt thereof:

(III)

wherein $R_2$ is selected from straight or branched $C_3$-$C_8$ alkyl, straight or branched $C_2$-$C_8$ alkenyl; straight or branched $C_2$-$C_8$ alkynyl; wherein said alkyl, alkenyl and alkynyl are each substituted by at least one group selected from —C(=O)NR$_3$R$_4$, —NHR$_5$ and —NR$_6$R$_7$;

$R_3$, $R_4$, $R_5$, $R_6$ and $R_7$ are each independently selected from H, straight or branched $C_1$-$C_{10}$ alkyl and aryl;

provided that when $R_2$ is a $C_2$ alkyl that $R_3$, $R_4$, $R_5$, $R_6$ and $R_7$ are each independently selected from straight or branched $C_1$-$C_{10}$ alkyl and aryl.

In some embodiments, a compound of formula (III) is:

The invention also encompasses the use of a compound of general formula (IV), including any stereoisomer and salt thereof:

(IV)

wherein $R_1$ is selected from H, OH, $C_1$-$C_{10}$ alkoxy, aryloxy, benzyloxy, halogen, straight or branched $C_1$-$C_5$ alkyl, straight or branched $C_2$-$C_6$ alkenyl; straight or branched $C_2$-$C_6$ alkynyl;

$R_2$ is selected from straight or branched $C_2$-$C_8$ alkyl, straight or branched $C_2$-$C_8$ alkenyl; straight or branched $C_2$-$C_8$ alkynyl; wherein said alkyl, alkenyl and alkynyl are each substituted by at least one group selected from —C(=O)O($C_1$-$C_5$alkyl), —C(=O)NR$_3$R$_4$, —NHR$_5$ and —NR$_6$R$_7$;

$R_3$, $R_4$, $R_5$, $R_6$ and $R_7$ are each independently selected from H, straight or branched $C_1$-$C_{10}$ alkyl and aryl; for the preparation of a medicament for the prevention, treatment or slowing the progression of a disease, disorder or condition including any symptoms thereof, selected from inflammatory disease, neurodegenerative disease, disease associated with at least one of oxidative stress, an immune response, release of NO and release of pro-inflammatory cytokines.

In some embodiments, a compound of the invention is selected from the following:

| Compound | AN-number | Structure |
|---|---|---|
| 4b | 1297 | |
| 4c | 1296 | |
| 4d | 1285 | |

-continued

| Compound | AN-number | Structure |
|---|---|---|
| 4f | 1279 | |
| 6b | 1299 | |
| 10g | 1276 | |
| 12a | 1284 | |
| 12b | 1298 | |
| 12g | 1280 | |
| 15a | 1292 | |

-continued

| Compound | AN-number | Structure |
|----------|-----------|-----------|
| 15b | 1295 | |
| 15d | 1287 | |
| 15e | 1294 | |
| 15h | 1293 | |
| 20 | 1282 | |

The invention further provides the use of a compound that is selected from the following:

| Compound | AN-number | Structure |
|----------|-----------|-----------|
| | 647 | |

-continued

| Compound | AN-number | Structure |
|----------|-----------|-----------|
| 4a | 1283 | |
| 4b | 1297 | |
| 4c | 1296 | |
| 4d | 1285 | |
| 4f | 1279 | |
| 6a | 1400 | |
| 6b | 1299 | |

-continued

| Compound | AN-number | Structure |
| --- | --- | --- |
| 10a | 1264 | |
| 10g | 1276 | |
| 12a | 1284 | |
| 12b | 1298 | |
| 12g | 1280 | |
| 15a | 1292 | |
| 15b | 1295 | |

-continued

| Compound | AN-number | Structure |
|---|---|---|
| 15d | 1287 | |
| 15e | 1294 | |
| 15h | 1293 | |
| 20 | 1282 | | for the preparation of a medicament for the prevention, treatment or slowing the progression of a disease, disorder or condition including any symptoms thereof, selected from inflammatory disease, neurodegenerative disease, disease associated with at least one of oxidative stress, an immune response, release of NO and release of pro-inflammatory cytokine.

The present invention also relates to pharmaceutical compositions comprising compounds of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragees or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

The invention also includes any salt of a compound of formula (I), including any pharmaceutically acceptable salt, wherein a compound of the invention has a net charge (either positive or negative) and at least one counter ion (having a counter negative or positive charge) is added thereto to form said salt. The phrase "pharmaceutically acceptable salt(s)", as used herein, means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), incorporated herein by reference.

When referring to "$C_1$-$C_{10}$ alkoxy" it should be understood to relate to an RO— moiety wherein R is a straight or branched $C_1$-$C_{10}$ alkyl. When referring to "aryloxy" it should be understood to relate to an RO— moiety wherein R is a $C_5$-$C_{12}$ aryl (either single or fused). When referring to "benzyloxy" it should be understood to relate to an RO— moiety wherein R is a benzyl. When referring to a "halogen" it should be understood to relate any one of F, Cl, Br, I. When referring to "straight or branched $C_1$-$C_5$ alkyl" it should be understood to relate to a hydrocarbon straight or branched chain wherein all carbon atoms are boned to each other and to the hydrogen atoms with a single sigma bond. When referring to "straight or branched $C_2$-$C_6$ alkenyl" it should be understood to relate to a hydrocarbon straight or branched chain wherein at least two carbon atoms are boned to each other with a double bond. When referring to "straight or branched $C_2$-$C_6$ alkynyl" it should be understood to relate to a hydrocarbon straight or branched chain wherein at least two carbon atoms are boned to each other with a triple bond.

It is to be understood that the compounds provided herein may contain one or more chiral centres. Such chiral centres may have a configuration of either the (R) or (S) configuration. Compositions provided herein comprising compounds of the invention may be enantiomerically pure (i.e. comprise a single enantiomer or diastereomer of a compound of the invention), or include stereoisomeric mixture of compounds of the invention (i.e. mixtures of enantiomenrs, such as a racemic mixture, or mixtures of diastereomers—such mixtures may be equimolar or non-equimolar).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 10 shows how AN1284 treatment reduces the size of renal cysts and in situ proliferation in TSC1-induced KO mice. Shown are representative slices of the kidney with imunohistochemical staining with Ki67 in three of the five mice. AN1284 reduced by more than 50% the number of positive nuclei compared to the treated mice.

FIG. 12A. Urine albumin-to-creatinine ratio (ACR) FIG. 12B. Serum urea levels. Data represent mean±SEM from 8-10 mice per group. Significantly different from vehicle treated control mice *p<0.05; significantly different from vehicle treated mice with STZ-induced diabetes # p<0.05.

FIG. 13A control mouse; FIG. 13B mouse with STZ induced nephropathy, FIG. 13C mouse with STZ induced diabetes that received AN1284.

FIG. 14A. Quantification of glomerular cross-sectional area. FIG. 14B. Quantification of mesangial expansion. Data represent mean±SEM from 8-10 mice per group. Significantly different from vehicle treated control mice *p<0.05; significantly different from vehicle treated mice with STZ-induced diabetes # p<0.05.

FIGS. 15A-15F shows mitigation by AN1284 of diabetes-induced renal injury, inflammation and fibrosis. Diabetic-induced increases in renal mRNA expression levels of: FIG. 15A. lipocalin 2. FIG. 15B. Timp1. FIG. 15C. IP-10. Fibrogenic markers, FIG. 15D collagen I. FIG. 15E collagen III. FIG. 15F. fibronectin 1, were significantly normalised by AN1284 (0.5 mg/kg, sc) treatment. Data represent mean±SEM from 8-10 mice per group. Significantly different from vehicle treated control mice *p<0.05; significantly different from vehicle treated mice with STZ-induced diabetes # p<0.05.

DETAILED DESCRIPTION OF EMBODIMENTS

Experimental Section

Figure 1:
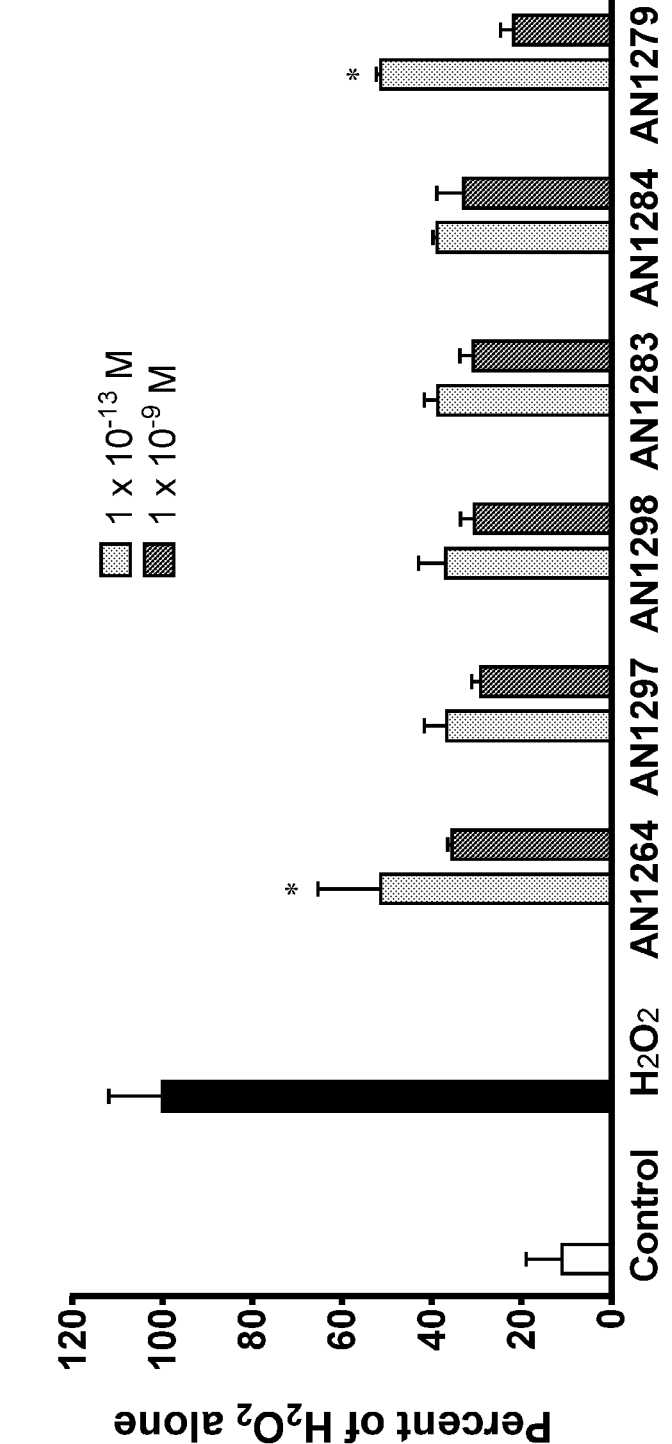
FIG. 1 shows the reduction by compounds in caspase 3 activity induced in macrophages by exposure to $H_2O_2$. Data represent the mean±SD from 4-6 replicates per concentration of each compound. All compounds significantly reduced caspase 3 activity $p<0.01$. Significantly different from same concentration of the other compounds * $p<0.05$.

General Remarks. $^1$H-NMR, $^{13}$C-NMR spectra were obtained on Bruker Avance-DPX-300, Avance-400, Avance-DMX-600 and Avance-III-700 spectrometers. Chemical shifts are expressed in ppm downfield from Me3Si (TMS) used as internal standard. The values are given in δ scale. The "t" is indicative of a multiplet similar to a triplet with second order characteristics. Mass spectra (MS) were obtained on a Varian Mat 731 spectrometer (CI[+]=chemical ionization). HRMS were obtained on AutoSpec spectrometer (Water company-UK) (CI[+] CH$_4$). Electron Spray ionization (ESI) was obtained on a Micromass Q-TOF Micro mass spectrometer (Micromass (Waters) UK). HRMS were obtained on Synapt ESI-Q-TOF (Water company-UK). Progress of the reactions was monitored by TLC on silica gel (Merck, Art. 5554). All the flash chromatographic procedures were carried out on silica gel (Merck, Art. 9385). All moisture sensitive reactions were carried out in flame-dried vessels. Melting points were determined on a Fisher-Johns apparatus. Commercially available compounds were used without further purification. The nomenclature of the compounds was given according to ChemDraw Ultra v. 13 and 14 (CambridgeSoft). The numbering on the chemical structures below is arbitrary and it serves only for spectral analysis. Commercial reagents were used without further purification.

Procedure A: N-Alkylation of indoles or indolines with methyl acrylate (Yeom, et al., 2007). To a stirred solution of an indole or an indoline (0.46 mmol), and methyl acrylate (0.7 mmol) in CH$_3$CN (2 mL) was added DBU (0.23 mmol). The mixture was stirred at 50° C. for 19-24 h, extracted with EtOAc, washed with 1N HCl or 1N KHSO$_4$ or saturated aqueous KHSO$_4$, dried over Na$_2$SO$_4$ and evaporated.

Procedure B: Reduction of indoles to indolines

Method I: (Yeom et al., 2007). To a solution of an indole (1 mmol) in AcOH (8 mL) at 0° C., was added NaBH$_3$CN (2 mmol). The mixture was stirred at room temperature from 2-16 h. The residue was extracted with EtOAc and saturated aqueous NaHCO$_3$, dried over Na$_2$SO$_4$ and evaporated.

Method II: (Yao et al., 2010). A solution of an indole (0.3 mmol) in TFA (4 mL) and Et$_3$SiH (0.8 mmol) was heated to 60° C. and stirred for 4.5 h. The residue was extracted with DCM and saturated aqueous NaHCO$_3$, dried over Na$_2$SO$_4$ and evaporated.

Method III: (Yanovsky et al., 2012). To a solution of an indole (0.3 mmol) in TFA (20 mL) at 0° C., was added NaBH$_4$ (1.5 mmol). The mixture was stirred at room temperature from 2-16 h and evaporated. The residue was extracted with EtOAc and saturated aqueous NaHCO$_3$, dried over Na$_2$SO$_4$ and evaporated.

Procedure C: N-Alkylation of indoles with acrylonitrile. (Roy et al., 2005). To a solution of an indole (17 mmol) in dioxane (20 mL) at 0° C. was added acrylonitrile (26 mmol) followed by the dropwise addition of Triton-B (0.8 mL). The resulting mixture was slowly allowed to warm to room temperature and was stirred for 20 h and was then evaporated. KHSO$_4$ 1 N was added dropwise to neutralize the basic catalyst, and the solution was extracted with EtOAc, dried over Na$_2$SO$_4$ and evaporated.

Procedure D: N-Alkylation of indoles with N-isopropylacrylamide. (Roy et al., 2006). To a stirred solution of an indole (7 mmol) in dioxane was added N-isopropylacrylamide (7 mmol) and KOH (8.4 mmol). The mixture was stirred at 50° C. from 18-72 h and was then filtered and evaporated.

Procedure E: Reduction of a nitrile (Amundsen et al., 1951). To a solution of a nitrile (n g) in anhydrous diethyl ether (60 mL) at 0° C. was slowly added LAH (n g). The resulting mixture was allowed to warm slowly to room temperature and was further stirred for 24 h. To the mixture was then added water n mL, n mL of 15% NaOH and 3n mL of water. The ether solution was filtered through celite and evaporated.

Procedure F: Reduction of amide or esters (Shirota et al., 2003). To a suspension of LiAlH$_4$ (n g) in anhydrous THF was added drop-wise a solution of an amide (n g) in anhydrous THF. The mixture was refluxed for 24 h for amide reduction or 1 h for ester reduction, cooled to room temperature. The reaction was worked up by addition of water n mL, n mL of 15% NaOH and 3n mL of water. The THF solution was filtered through celite and evaporated. To the residue was added 1N of HCl and the solution was extracted with EtOAc. To the aqueous layer was added saturated Na$_2$CO$_3$ until reaching pH=10 and the solution was extracted with EtOAc. The organic layer was then dried over Na$_2$SO$_4$ and evaporated to give the product.

Scheme 1. Synthesis of methyl 3-(indolin-1-yl)propanoates a) $CH_2 = CHCOOMe/MeCN/DBU/50°$ C.;
b) $NaCNBH_3/AcOH$ or $Et_3SiH/TFA$ or $NaBH_4/TFA$;
c) HCl (g)/diethyl ether ot p-TSA/t-butyl methyl ether;
d) LAH/THF/HCl Indolines substituted with a methyl propionyl chain at position 1 were prepared from the corresponding indoles 1 or indoline 5a upon treatment with methyl acrylate/DBU. Reduction of the N-alkylated indoles 2a-d,f with NaBH3CN/AcOH. (Yeom et al., 2012), or $NaBH_4$/TFA (Yanovsky et al., 2012) or $Et_3SiH$/TFA (Yao et al., 2010), gave the corresponding indolines 3a-d,f that were isolated as hydrochlorides 4a-c or p-toluenesulfonate salts 4d,f The salts of the 1-(3-aminopropyl) derivatives 10a,g were prepared from the corresponding indoles 1a,g upon N-alkylation with acrylonitrile, followed by initial reduction of the indolic to the indolinic system and subsequent reduction of the CN to the corresponding aminomethyl group, and the final products were isolated as p-toluenesulfonate salts 10a,g (Scheme 2).

Scheme 2. Synthesis of 3-(indolin-1-yl)propan-1-amines (a) $CH_2 = CHCN$/Triton B/dioxane, $0°$ C. -> rt;
(b) $NaCNBH_3$/AcOH, rt;
(c) $LiAlH_4$/diethylether;
(d) p-TSA/t-butyl methyl ether

65

(Scheme 1). In addition, ester reduction of 3a,b followed by acidification gave the alcohols 6a,b.

An unexpected reaction took place when an attempt was made to debenzylate 9g under catalytic hydrogenation conditions in a Parr apparatus. Apparently, the hydrogenator contained traces of acetone, which condensed with the amine to give the intermediate imine that underwent further reduction and acidification to give the N-isopropylamino derivative 12g (Scheme 3). An alternative approach to the synthesis of the N-isopropylamino derivatives 12a,b, involved the N-alkylation of indoles 1 with N-isopropylamino acrylamide to give 13a,b, followed by reduction of the indole to the indoline and reduction of the amide to the amine with subsequent acidification (Scheme 4).

Scheme 3. Synthesis of 1-(3-Isopropylamino)propyl)indolines

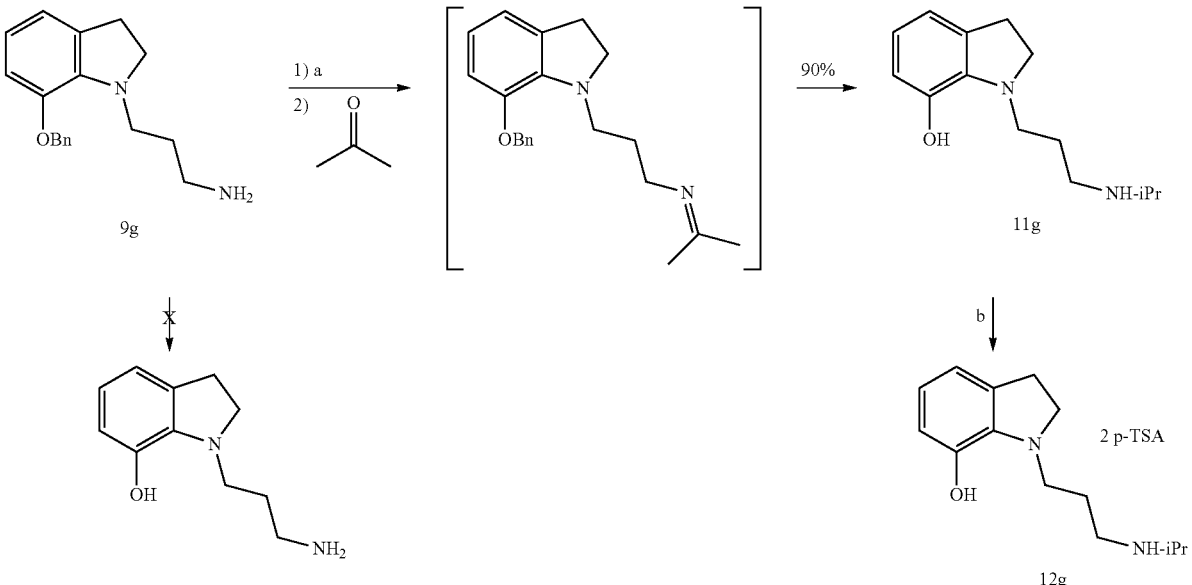

(a) H₂/10% Pd/C/MeOH, 4 atm (and traces of acetone in the hydrogenator);
(b) p-TSA/t-butyl methyl ether;

Scheme 4: Synthesis of 3-(indolin-1-yl)-N-sopropylpropanamides 15 and 3-(indolin-1-yl)-N-isopropylpropan-1-amines 12

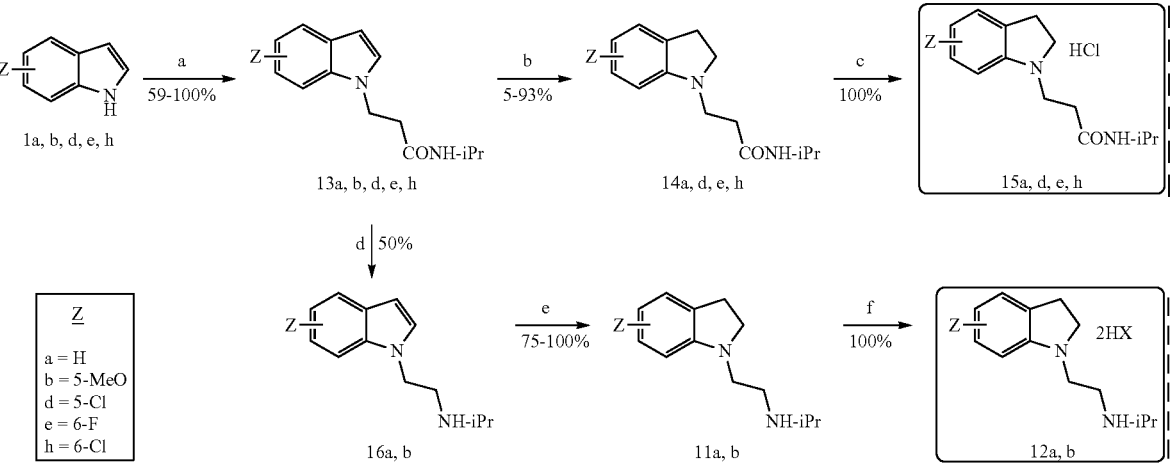

a) CH₂ = CH-CONH-i-Pr/KOH/Dioxane;
b) TFA/NaBH₄;
c) HCl (g)/Diethyl ether or HCl 3N/EtOAc;
d) LAH/THF;
e) NaCNBH₃/AcOH or TFA/NaBH₄;
f) HCl (g)/Diethyl ether or p-TSA/t-butyl methyl ether A 3-aminopropyl derivative substituted at position 3 of the indoline system 20, was obtained upon amidation of IPA to give amide 17, which underwent two reductive steps and acidification of amine 19 (Scheme 5).

Methyl 3-(5-Methoxy-1H-indol-1-yl)propanoate, (2b). Compound 2b synthesised from 5-methoxyindole by Procedure A, was isolated as an orange oil in 94% yield. $^1$H-NMR (300 MHz, CDCl$_3$) ppm δ 7.18 (d, J=9.0 Hz, 1H), 7.07-7.04

Scheme 5. Synthesis of 3-(indolin-3-yl)propan-1-amine di-p-toluenesulfonate, 20 a) CDI/NH$_4$OH;
b) LAH/THF;
c) Et$_3$SH/TFA;
d) p-TSA

Preparation Procedures of Specific Compounds of the Invention

Methyl 3-(1H-Indol-1-yl)propanoate (2a). Compound 2a synthesised from indole by Procedure A, was isolated as a yellow oil in approximately quantitative yield. $^1$H-NMR (400 MHz, CDCl$_3$) ppm δ 7.60 (d, J=8 Hz, 1H), 7.30 (d, J=8.4 Hz, 1H), 7.19 (t, J=8.0 Hz, 1H), 7.11-7.06 (m, 2H), 6.45 (d, J=3.2 Hz), 4.38 (t, J=6.8 Hz), 3.61 (s, 3H), 2.76 (t, J=6.8 Hz, 2H); $^{13}$C-NMR (100 MHz, CDCl$_3$) ppm δ 171.67, 135.69, 128.78, 127.94, 121.69, 121.11, 119.57, 109.12, 101.65, 51.90, 41.80, 34.76.

(m, 2H), 6.88-6.83 (m, 1H), 6.38-6.36 (m, 1H), 4.34 (t, J=6.9 Hz, 2H), 3.80 (s, 3H), 3.60 (s, 3H), 2.74 (t, J=6.9 Hz, 2H); $^{13}$C-NMR (75 MHz, CDCl$_3$) ppm δ 171.66, 154.08, 130.93, 129.06, 128.43, 111.92, 109.82, 102.68, 101.13, 55.79, 51.85, 41.90, 34.78; MS (TOF MS ES$^+$) m/z 234 (MH$^+$)

Methyl 3-(6-Methyl-1H-indol-1-yl)propanoate, (2c). Compound 2c synthesised from 6-methylindole by Procedure A, was isolated as a yellow oil in 81% yield. $^1$H-NMR (400 MHz, CDCl$_3$) ppm δ 7.42 (d, J=8.0 Hz, 1H), 6.99 (s, 1H), 6.87-6.83 (m, 1H), 6.81 (d, J=3.2 Hz, 1H), 6.32 (d, J=3.2 Hz, 1H), 4.04 (t, J=6.8 Hz, 2H), 3.39 (s, 3H), 2.46 (t, J=6.8 Hz, 2H), 2.40 (s, 3H); $^{13}$C-NMR (100 MHz, CDCl$_3$) ppm δ 171.26, 135.79, 130.86, 126.97, 126.32, 121.01, 120.37, 108.81, 100.98, 51.17, 41.08, 34.09, 21.46.

Methyl 3-(5-Chloro-1H-indol-1-yl)propanoate, (2d). Compound 2d synthesised from 5-chloroindole by Procedure A, was isolated as an orange oil in 86% yield. $^{1}$H-NMR (300 MHz, CDCl$_{3}$) ppm δ 7.51 (d, J=1.8 Hz, 1H), 7.15-7.03 (m, 3H), 6.34 (d, J=3.3 Hz, 1H), 4.26 (t, J=6.9 Hz, 2H), 3.55 (s, 3H), 2.66 (t, J=6.9 Hz, 2H); $^{13}$C-NMR (75 MHz, CDCl$_{3}$) ppm δ 171.34, 133.94, 129.53, 129.17, 124.97, 121.64, 120.15, 110.08, 101.11, 51.73, 41.67, 34.45; MS (TOF MS ES+) m/z 238 (MH$^{+}$), 276 (MK)$^{+}$ Methyl 3-(6-(Benzyloxy)-1H-indol-1-yl)propanoate, (2f). Compound 2f synthesised from 6-benzyloxyindole by Procedure A, was filtered through a short silica gel column, eluted with EtOAc-hexane (1:3). Evaporation of the filtrate gave the product as a pink solid, mp 45° C., in 94% yield. $^{1}$H-NMR (200 MHz, CDCl$_{3}$) ppm δ 7.55-7.3 (m, 6H), 7.03 (d, J=3.2 Hz, 2H), 6.93-6.84 (m, 2H), 6.43 (d, J=3.2 Hz, 1H), 5.15 (s, 2H), 4.39 (t, J=6.8 Hz, 2H), 3.68 (s, 3H), 2.80 (t, J=6.8 Hz, 2H); $^{13}$C-NMR (75 MHz, CDCl$_{3}$) ppm δ 171.58, 155.46, 137.49, 136.35, 128.50, 127.81, 127.43, 126.96, 123.29, 121.59, 109.98, 101.56, 94.61, 70.77, 51.79, 41.71, 34.49; MS (CI$^{+}$) m/z 309.134 (M$^{+}$), 310.142 (MH$^{+}$); HRMS calcd. for C$_{19}$H$_{19}$NO$_{3}$ (M$^{+}$, CI$^{+}$/CH$_{4}$) 309.1365 found 309.1342, for C$_{19}$H$_{20}$NO$_{3}$ (MH$^{+}$, CI$^{+}$/CH$_{4}$) 310.1443 found 310.1416.

Methyl 3-(Indolin-1-yl)propanoate, (3a). Compound 3a synthesised from 2a by Procedure B method I or from indoline 5a by Procedure A, was isolated as a yellow oil in 83 or 76% yield, respectively. $^{1}$H-NMR (300 MHz, CDCl$_{3}$) ppm δ 7.10-6.99 (m, 2H), 6.617 (t, J=7.2 Hz, 1H), 6.47 (d, J=8.1 Hz, 1H), 3.63 (s, 3H), 3.36 (t, J=6.9 Hz, 2H), 3.28 (t, J=8.1 Hz, 2H), 2.89 (t, J=8.1 Hz, 2H), 2.50 (t, J=6.9 Hz, 2H);

$^{13}$C-NMR (75 MHz, CDCl$_{3}$) ppm δ 172.38, 151.63, 129.70, 127.15, 124.25, 117.66, 106.86, 52.85, 51.44, 44.87, 32.05, 28.38.

Methyl 3-(5-Methoxyindolin-1-yl)propanoate, (3b). Compound 3b prepared from 2b by Procedure B method II, was purified by elution through a short silica gel column with EtOAc-hexane (1:10→1:7), and was isolated as a yellow oil in 57% yield. $^{1}$H-NMR (300 MHz, CDCl$_{3}$) ppm δ 6.89 (d, J=8.4 Hz, 1H), 6.79-6.72 (m, 2H), 3.77 (s, 3H), 3.70 (s, 3H), 3.55 (t, J=7.2 Hz, 2H), 3.50 (t, J=6.9 Hz, 2H), 3.07 (t, J=7.2 Hz, 2H), 2.73 (t, J=6.9 Hz, 2H); $^{13}$C-NMR (75 MHz, CDCl$_{3}$) ppm δ 171.76, 156.74, 140.49, 133.76, 113.17, 113.06, 111.66, 55.97, 53.88, 52.09, 48.73, 31.07, 28.70; MS (TOF MS ES+) m/z 236

Methyl 3-(6-methylindolin-1-yl)propanoate, (3c). Compound 3c synthesised from 2c by Procedure B method III, was isolated as a yellow oil, in approximately quantitative yield. $^{1}$H-NMR (300 MHz, CD$_{3}$OD) ppm δ 6.88 (d, J=7.2 Hz, 1H), 6.47 (d, J=7.2 Hz, 1H), 6.38 (s, 1H), 3.64 (s, 3H), 3.31 (t, J=6.9 Hz, 2H), 3.22 (t, J=8.4 Hz, 2H), 2.79 (t, J=8.1 Hz, 2H), 2.55 (t, J=6.9 Hz, 2H), 2.22 (s, 3H); $^{13}$C-NMR (75 MHz, CD$_{3}$OD) ppm δ 174.39, 152.54, 137.93, 128.50, 125.04, 120.45, 109.82, 54.25, 52.14, 46.57, 32.80, 28.86, 21.72.

Methyl 3-(5-Chloroindolin-1-yl)propanoate, (3d). Compound 3d synthesised from 2d by Procedure B method III, was isolated as a red-orange oil in approximately quantitative yield. $^{1}$H-NMR (300 MHz, CDCl$_{3}$) ppm δ 6.96-6.93 (m, 2H), 6.35 (d, J=9.0 Hz, 1H), 3.65 (s, 3H), 3.34 (t, J=6.9 Hz, 2H), 3.31 (t, J=8.4 Hz, 2H), 2.86 (t, J=8.4 Hz, 2H), 2.55 (t, J=7.2 Hz, 2H); $^{13}$C-NMR (75 MHz, CDCl$_3$) ppm δ 172.40, 150.42, 131.69, 126.80, 124.47, 122.00, 107.35, 52.95, 51.59, 44.82, 32.00, 28.19; MS (ES+) m/z 240 (MH$^+$)

Methyl 3-(6-(Benzyloxy)indolin-1-yl)propanoate, (3f). Compound 3f synthesised from 2f by Procedure B method I, and gave the product as a yellow oil, in 95% yield. $^1$H-NMR (300 MHz, CDCl$_3$) ppm δ 7.44-7.23 (m, 5H), 6.90 (d, J=8.1 Hz, 1H), 6.23 (dd, J=8.1, 2.1 Hz, 1H), 6.17 (d, J=2.1 Hz, 1H) 4.98 (s, 2H), 3.65 (s, 3H), 3.39-3.30 (m, 4H), 2.85 (t, J=8.2 Hz, 2H), 2.56 (t, J=7.0 Hz, 2H); $^{13}$C-NMR (75 MHz, CDCl$_3$) ppm δ 172.80, 159.32, 153.05, 137.40, 128.46, 127.75, 127.62, 124.43, 122.56, 102.65, 95.56, 70.12, 53.54, 51.74, 44.74, 32.10, 27.77; MS (EI$^+$) m/z 311.152 (M$^+$), 312.155 (MH$^+$); HRMS calcd. for C$_{19}$H$_{21}$NO$_3$(M$^+$, EI$^+$) 311.1521 found 311.1524.

Methyl 3-(Indolin-1-yl)propanoate Hydrochloride, (4a AN1283). The hydrochloride salt 4a was prepared by addition of a solution of HCl (gas)/ether to 3a and was isolated as an orange hygroscopic solid in approximately quantitative yield. $^1$H-NMR (300 MHz, CD$_3$OD) ppm δ 7.63-7.60 (m, 1H), 7.54-7.47 (m, 3H), 4.00 (t, J=7.5 Hz, 2H), 3.86 (t, J=6.9 Hz, 2H), 3.74 (s, 3H), 3.37 (t, J=7.5 Hz, 2H), 2.97 (t, J=6.9 Hz, 2H; $^{13}$C-NMR (75 MHz, CD$_3$OD) ppm δ 172.10, 141.41, 136.65, 131.77, 129.94, 127.68, 119.88, 55.54, 53.33, 52.84, 30.25, 28.92.

Methyl 3-(5-Methoxyindolin-1-yl)propanoate Hydrochloride, (4b AN1297). Compound 4b was prepared by addition of HCl (g) to 3b (0.11 g/0.47 mmol) in dry diethyl ether (12 mL). The precipitate was isolated as a dark red oil in approximately quantitative yield. $^1$H-NMR (300 MHz, CD$_3$OD) ppm δ 7.52 (d, J=8.7 Hz, 1H, 7.06-6.98 (m, 2H), 4.02 (t, J=7.5 Hz, 2H), 3.84 (s, 3H), 3.81 (t, J=7.2 Hz, 2H), 3.73 (s, 3H), 3.34 (t, J=7.5 Hz, 2H), 2.97 (t, J=7.2 Hz, 2H); $^{13}$C-NMR (75 MHz, CD$_3$OD) ppm δ 172.01, 163.20, 138.55, 133.45, 121.00, 115.89, 112.13, 56.48, 56.05, 53.64, 52.87, 30.20, 29.11; MS (TOF MS ES+) m/z 236.

Methyl 3-(6-Methylindolin-1-yl)propanoate Hydrochloride, (4c AN1296). The hydrochloride of 4c obtained by addition of a solution of HCl (gas)/ether to 3c was isolated as a yellow oil in approximately quantitative yield. $^1$H-NMR (300 MHz, CD$_3$OD) ppm δ 7.46 (s, 1H), 7.38-7.30 (m, 2H), 4.00 (t, J=7.5 Hz, 2H), 3.84 (t, J=7.2 Hz, 2H), 3.70 (s, 3H), 3.30 (t, J=7.5 Hz, 2H), 3.00 (t, J=6.9 Hz, 2H), 2.40 (s, 3H); $^{13}$C-NMR (75 MHz, CD$_3$OD) ppm δ 171.75, 140.93, 140.55, 133.50, 132.68, 127.12, 120.34, 55.53, 53.19, 52.79, 30.16, 28.52, 21.34.

Methyl 3-(5-Chloroindolin-1-yl)propanoate p-Toluenesulfonate, (4d AN1285). Compound 4d was prepared by addition of p-TSA to a solution of 3d in t-butyl methyl ether. The ethereal solution was evaporated to give 4d as a brown oil that was found that the salt contained a ~50% excess of p-TSA, detected by NMR. $^1$H-NMR (300 MHz, CD$_3$OD) ppm δ 7.62 (d, J=8.4 Hz, 4H), 7.53 (d, J=8.4 Hz, 1H), 7.35-7.30 (m, 2H), 3.98 (t, J=7.5 Hz, 2H), 3.79 (t, J=7.2 Hz, 2H), 3.65 (s, 3H), 3.24 (t, J=7.5 Hz, 2H), 2.91 (t, J=7.2 Hz, 2H), 2.29 (s, 6H); $^{13}$C-NMR (75 MHz, CD$_3$OD) ppm 6171.53, 142.60, 141.73, 139.59, 138.86, 137.05, 129.76, 129.62, 127.39, 126.60, 121.47, 55.77, 53.27, 52.72, 30.03, 28.65, 27.14, 21.32; MS (ES$^+$) m/z 240 (MH$^+$).

107A

107B

Methyl 3-(6-(Benzyloxy)indolin-1-yl)propanoate p-Toluenesulfonate, (4f AN1279). Compound 4f was prepared by addition of p-TSA (0.13 g, 0.7 mmol) to 3f (0.21 g, 0.7 mmol) in t-butyl methyl ether (10 mL) to give the product as a hygroscopic white solid, having 2 equivalents of p-TSA. It should be noted that an H→D exchange took place when 4f was dissolved in $CD_3OD$ in an NMR tube. The exchange was detected by NMR already after 5 min, and was shown to take place at position 5 to give 4f-A, and partly at both positions 5 and 7 to give 4f-B. $^1$H-NMR (600 MHz, $CD_3OD$) ppm δ 7.66 (d, J=8.4 Hz, 4.5H), 7.43 (d, J=7.2 Hz, 2H), 7.36 (t, J=7.2 Hz, 2H), 7.33 (s, 1H), 7.32-7.29 (m, 1H), 7.21 (d, J=8.4 Hz, 4.5H), 7.15 (s, 0.4H), 5.10 (s, 2H), 3.93 (t, J=8.2 Hz, 2H), 3.77 (t, J=8.2 Hz, 2H), 3.71 (s, 3H), 3.20 (t, J=8.2 Hz, 2H), 2.86 (t, J=8.2 Hz, 2H), 2.35 (s, 7H); $^{13}$C-NMR (150 MHz, $CD_3OD$) ppm δ 172.30, 160.69, 143.50, 143.01, 141.75, 138.00, 129.84, 129.62, 129.15, 128.76, 127.88, 127.82, 126.97, 105.67, 71.70, 56.26, 52.91, 52.82, 30.40, 28.28, 21.33; MS (for SZ-I-107) (EI$^+$) m/z 311.152 (M$^+$), 312.155 (MH$^+$); HRMS calcd. for $C_{19}H_{21}NO_3$(M$^+$, EI$^+$) 311.1521 found 311.1524 and calcd for $C_{19}H_{21}NO_3Na$ (MNa$^+$, EI$^+$) 334.1419 found 334.1422.

3-(Indolin-1-yl)propan-1-ol, (AN1400 free base). (Yushi et al., 2015) Compound 6a free base prepared from 3a by Procedure F, was isolated as a dark oil in 98% yield. $^1$H-NMR (300 MHz, CDCl$_3$) ppm δ 7.04-6.99 (m, 2H), 6.63 (t, J=7.5 Hz, 1H), 6.49 (d, J=7.5 Hz, 1H), 4.04 (bs, 1H), 3.66 (t, J=6.0 Hz, 2H), 3.25 (t, J=8.1 Hz, 2H), 3.10 (t, J=6.3 Hz, 2H), 2.88 (t, J=8.1 Hz, 2H), 1.78 (quint, J=6.3 Hz, 2H); $^{13}$C-NMR (75 MHz, CDCl$_3$) ppm δ 152.33, 129.94, 127.07, 124.20, 117.83, 107.35, 60.63, 53.24, 46.88, 29.78, 28.35; MS (ES$^+$) m/z 178.2 (MH$^+$).

3-(5-Methoxyindolin-1-yl)propan-1-ol, (6b free base). Compound 6b free base prepared from 3b by Procedure F was isolated as a yellow oil in 85% yield. $^1$H-NMR (300 MHz, CDCl$_3$) ppm δ 6.72 (s, 1H), 6.63-6.59 (m, 1H), 6.48-6.45 (m, 1H), 3.74 (t, J=6.0 Hz, 2H), 3.70 (s, 3H), 3.22 (t, J=8.1 Hz, 2H), 3.06 (t, J=6.6 Hz, 2H), 2.87 (t, J=7.8 Hz, 2H), 1.79 (quint, J=6.6 Hz, 2H); $^{13}$C-NMR (75 MHz, CDCl$_3$) ppm δ 153.14, 146.69, 131.78, 111.70, 111.70, 108.34, 61.49, 55.79, 54.23, 48.97, 29.82, 28.76; MS (ES$^+$) m/z 208 (MH$^+$); HRMS calcd. for $C_{12}H_{17}NO_2$ (MH$^+$, ES$^+$) 208.1332 found 208.1333.

3-(Indolin-1-yl)propan-1-ol Hydrochloride, (6a AN1400). Compound 6a was prepared by addition of a solution of HCl (gas)/ether to 6a free base and was isolated as a greyish hygroscopic solid in approximately quantitative yield. $^1$H-NMR (600 MHz, CD$_3$OD) ppm δ 7.61 (d, J=7.8 Hz, 1H), 7.53-7.52 (m, 2H), 7.51-7.48 (m, 1H), 4.01 (bt, 2H), 3.74 (t, J=6.0 Hz, 2H), 3.67 (bt, 2H), 3.37 (t, J=7.8 Hz, 2H), 2.02 (quint, J=7.2 Hz, 2H); $^{13}$C-NMR (150 MHz, CD$_3$OD) ppm δ 141.66, 136.68, 131.79, 129.96, 127.71, 119.97, 60.00, 56.17, 55.50, 29.00, 28.48; MS (ES$^+$) m/z 178.2 (MH$^+$).

3-(5-Methoxyindolin-1-yl)propan-1-ol Hydrochloride, (6b AN1299 hydrochloride). Compound 6b was prepared by addition of a solution of HCl (gas)/ether to 6b free base and was isolated as a brown hygroscopic solid in approximately quantitative yield. $^1$H-NMR (700 MHz, CD$_3$OD, at 275° K.) ppm δ 7.53 (d, J=9.1 Hz, 1H), 7.05 (d, J=2.1 Hz, 1H), 6.97 (dd, J=9.1, 2.8 Hz, 1H), 4.16 (br, 1H), 3.9-3.8 (br, 2H), 3.82 (s, 3H), 3.71 (t, J=6.3 Hz, 2H), 3.45 (br, 1H), 3.36 (br, 1H), 3.27 (br, 1H), 2.07 (br, 1H), 1.98 (br, 1H); $^{13}$C-NMR (176 MHz, CD$_3$OD, 275° K.) ppm δ 162.66, 138.35, 133.53, 120.92, 115.542, 111.80, 59.58, 56.37, 55.73, 55.45, 29.03, 28.33; MS (ES$^+$) m/z 208 (MH$^+$); HRMS calcd. for $C_{12}H^{17}NO_2$(MH$^+$, ES$^+$) 208.1332 found 208.1333.

3-(1H-Indol-1-yl)propanenitrile, (7a). (Wittig et al., 1958), Compound 7a was synthesised from indole by Procedure C, and was isolated as yellow oil in approximately quantitative yield. $^1$H-NMR (300 MHz, CDCl$_3$) ppm δ 7.59 (dd, J=7.8, 0.9 Hz, 1H) 7.20-7.13 (m, 2H), 7.13-7.07 (m, 1H), 6.98 (d, J=3.0 Hz, 1H), 6.47 (d, J=3.0 Hz, 1H), 4.11 (t, J=6.6 Hz, 2H), 2.49 (t, J=6.6 Hz, 2H); $^{13}$C-NMR (75 MHz, CDCl$_3$) ppm δ 135.18, 128.67, 127.47, 121.91, 121.51, 119.88, 117.45, 108.75, 102.35, 41.58, 118.72; MS (ES$^+$) m/z 170.085 (M$^+$), 171.084 (MH$^+$); HRMS calcd. for C$_{11}$H$_{10}$N$_2$(M$^+$, EI$^+$) 170.0844 found 170.0853.

3-(7-(Benzyloxy)-1H-indol-1-yl)propanenitrile, (7g). Compound 7g prepared from 7-benzyloxyindole by Procedure C, was purified by crystallisation from DCM-ether, and was isolated as a bright orange solid, mp 69-71° C., in approximately quantitative yield.

$^1$H-NMR (400 MHz, CDCl$_3$) ppm δ 7.47-7.35 (m, 5H), 7.24 (dd, J=8.0, 0.8 Hz, 1H), 7.02 (t, J=8.0 Hz, 1H), 7.01 (d, J=3.2 Hz, 1H), 6.75 (d, J=8.0 Hz, 1H), 6.47 (d, J=3.2 Hz, 1H), 5.17 (s, 2H), 4.56 (t, J=6.8 Hz, 2H), 2.70 (t, J=6.8 Hz, 2H); $^{13}$C-NMR (100 MHz, CDCl$_3$) ppm δ 146.34, 136.60, 131.69, 129.14, 128.97, 128.55, 129.34, 125.00, 120.68, 117.59, 114.49, 103.82, 102.66, 70.69, 45.28, 20.98; MS (EI$^+$) m/z 276.123 (M$^+$), 277.133 (MH$^+$), 185.059 (M-Bn); HRMS calcd. for C$_{18}$H$_{16}$N$_2$O (M$^+$, EI$^+$) 276.1263 found 276.1226.

3-(Indolin-1-yl)propanenitrile, (8a). (Astil and Boekelheide 1958). Compound 8a synthesised from 7a using Procedure B Method I, was isolated as a yellow oil in approximately quantitative yield. $^1$H-NMR (300 MHz, CDCl$_3$) ppm δ 7.12-7.07 (m, 2H), 6.72 (t, J=7.5 Hz, 1H), 6.48 (d, J=7.8 Hz, 1H), 3.46-3.39 (m, 4H), 3.00 (t, J=8.4 Hz, 2H), 2.59 (t, J=6.9 Hz, 2H); $^{13}$C-NMR (75 MHz, CDCl$_3$) ppm δ 150.76, 129.74, 128.54, 124.64, 118.64, 118.34, 106.67, 52.90, 45.17, 28.43, 11.01; MS (EI$^+$) m/z 172.106 (M$^+$), 173.109 (MH$^+$); HRMS calcd. for C$_{11}$H$_{12}$N$_2$(M$^+$, EI$^+$) 172.1000 found 172.1061.

3-(7-(Benzyloxy)indolin-1-yl)propanenitrile, (8g). Compound 8g synthesised from 7g by Procedure B Method I, was isolated as a yellow oil in approximately quantitative yield.

$^1$H-NMR (300 MHz, CDCl$_3$) ppm δ 7.46-7.26 (m, 5H), 6.77-6.63 (m, 3H), 4.98 (s, 2H), 3.63 (t, J=6.9 Hz, 2H), 3.40 (t, J=8.7 Hz, 2H), 2.94 (t, J=8.7 Hz, 2H), 2.42 (t, J=6.9 Hz, 2H); $^{13}$C-NMR (75 MHz, CDCl$_3$) ppm δ 144.98, 138.69, 136.69, 132.04, 128.58, 128.03, 127.53, 119.83, 118.99, 118.01, 112.11, 70.63, 54.08, 47.23, 29.06, 16.67; MS (EI$^+$) m/z 278.146 (M+), 279.156 (MH$^+$); HRMS calcd. for C$_{18}$H$_{18}$N$_2$O (M$^+$, EI$^+$) 278.1419 found 278.1462.

3-(Indolin-1-yl)propan-1-amine, (9a). (a) Petrovna et al., 2010; b) Shapiro et al., 1959). Compound 9a synthesised from 8a by Procedure E, was isolated as a yellow oil in 68% yield. $^1$H-NMR (300 MHz, CDCl$_3$) ppm δ 6.90-6.86 (m, 2H), 6.48 (t, J=7.2 Hz, 1H), 6.29 (t, J=7.2 Hz, 1H), 3.09 (t, J=8.1 Hz, 1H), 2.87 (t, J=6.9 Hz, 1H), 2.74 (t, J=8.1 Hz, 2H), 2.50 (t, J=6.9 Hz, 2H), 1.47 (t, J=7.2 Hz, 2H); $^{13}$C-NMR (75 MHz, CDCl$_3$) ppm 6152.02, 129.84, 126.75, 124.02, 116.99, 106.43, 52.63, 48.44, 39.43, 30.42, 28.03; MS (EI$^+$) m/z 176.134 (M$^+$); HRMS calcd. for C$_{11}$H$_{16}$N$_2$ (M$^+$, EI$^+$) 176.1313 found 176.1337.

3-(7-(Benzyloxy)indolin-1-yl)propan-1-amine, (9g). Compound 9g was prepared from 8g by Procedure E, and was isolated as a yellow oil in approximately quantitative yield.

$^1$H-NMR (300 MHz, CDCl$_3$) ppm δ 7.50-7.17 (m, 5H), 6.83-6.60 (m, 3H), 4.99 (s, 2H), 3.41 (t, J=6.9 Hz, 2H), 3.33 (t, J=8.4 Hz, 2H), 2.95 (t, J=8.4 Hz, 2H), 2.61 (t, J=6.9 Hz, 2H), 1.87 (bs, 2H), 1.61 (quint, J=6.9 Hz, 2H); $^{13}$C-NMR (75 MHz, CDCl$_3$) ppm δ 145.44, 140.73, 137.17, 132.35, 128.55, 128.04, 127.79, 119.25, 118.02, 112.42, 70.82, 53.91, 49.18, 39.79, 31.54, 29.23; MS (ES$^{+)}$ $^{m/z}$ 283 (M$^+$); HRMS calcd. for C$_{18}$H$_{22}$N$_2$ONa (M$^+$, ES$^+$) 305.1630 found 305.1626.

3-(Indolin-1-yl)propanenitrile di-p-Toluenesulfonate, (10a AN1264). Compound 10a was prepared by addition of p-TSA (4.3 g, 22 mmol) to 9a (2 g, 11 mmol) in t-butyl methyl ether (60 mL). The precipitate was crystallized from DCM-ether and was isolated as a hygroscopic white solid, which contained an approximate 20% excess of p-TSA detected by NMR. $^1$H-NMR (300 MHz, CD$_3$OD) ppm δ 7.66 (d, J=8.1 Hz, 4H), 7.58 (bd, J=7.8 Hz, 1H), 7.54-7.37 (m, 3H), 7.2 (d, J=8.1 Hz, 4H), 3.97 (t, J=7.8 Hz, 2H), 3.65 ("t", J=8.1 Hz, 2H), 3.29 (m, 2H), 3.09 (t, J=7.5 Hz, 2H), 2.34 (s, 6H), 3.09 (quint, J=8.1 Hz, 2H); $^{13}$C-NMR (75 MHz, CD$_3$OD) ppm δ 143.14, 141.98, 140.91, 136.63, 131.97, 129.96, 127.68, 126.90, 120.17, 55.40, 54.60, 37.80, 28.97, 24.01, 21.34; MS (EI$^+$) m/z 176.137 (M$^+$), 177.142 (MH$^+$); HRMS calcd. for C$_{11}$H$_{16}$N$_2$(M$^+$, EI$^+$) 176.1313 found 176.1370.

3-(7-(Benzyloxy)indolin-1-yl)propan-1-amine di-p-Toluenesulfonate, (10g AN1276). Compound 10g was prepared by addition of p-TSA to a solution of 9g in t-butyl methyl ether. The ethereal solution was evaporated and 10g was crystallized from DCM-ether as a hygroscopic white solid in approximately quantitative yield. $^1$H-NMR (300 MHz, CD$_3$OD) ppm δ 7.69-7.65 (m, 4H), 7.52-7.33 (m, 6H), 7.20-7.14 (m, 5H), 7.03 (dd, J=7.5, 0.6 Hz, 1H), 4.01 (t, J=7.5 Hz, 2H), 3.60 ("t", J=7.2 Hz, 2H), 3.35-3.30 (m, 2H), 2.96 (t, J=7.5 Hz, 2H), 2.35 (s, 6H), 2.12-2.06 (m, 2H); $^{13}$C-NMR (75 MHz, CD$_3$OD) ppm δ 151.32, 143.28, 141.85, 138.83, 137.13, 133.91, 129.90, 129.82, 129.55, 129.08, 127.98, 126.86, 119.13, 113.67, 72.12, 66.84, 55.44, 54.01, 37.80, 29.32, 23.78, 21.31, 15.44.

3-(Indolin-1-yl)-N-isopropylpropan-1-amine, (11a). Compound 11a prepared from 16a by Procedure B method III, was isolated as a brown oil, in approximately quantitative yield. $^1$H-NMR (300 MHz, CDCl$_3$) ppm δ 7.05-7.00 (m, 2H), 6.64-6.59 (m, 1H), 6.46-6.43 (m, 1H), 3.29 (t, J=8.4 Hz, 2H), 3.07 (t, J=7.2 Hz, 2H), 2.91 (t, J=8.4 Hz, 2H), 2.77 (septet, J=6.3 Hz, 1H), 1.74 (quint, J=7.2 Hz, 2H), 1.04 (d, J=6.3 Hz, 6H); $^{13}$C-NMR (75 MHz, CDCl$_3$) ppm δ 152.56, 129.88, 127.17, 124.28, 117.40, 106.87, 53.11, 48.70, 47.59, 45.38, 28.46, 28.10, 22.79.

N-Isopropyl-3-(5-methoxyindolin-1-yl)propan-1-amine, (11b). Compound 11b synthesised from 16b by Procedure B method I, was isolated as a yellow oil in 75% yield.

$^1$H-NMR (300 MHz, CDCl$_3$) ppm δ $^1$H-NMR (300 MHz, CDCl$_3$) ppm δ 6.72 (s, 1H), 6.63-6.60 (m, 1H), 6.43-6.40 (m, 1H), 3.71 (s, 3H), 3.25 (t, J=8.1, 2H), 3.02 (t, J=6.9, 2H), 2.89 (t, J=8.1, 2H), 2.82 (septet, J=6.3 Hz, 1H), 2.72 (t, J=6.9, 2H), 2.512-2.493 (m, 2H), 1.78 (quint, J=7.2 Hz, 2H), 1.06 (d, J=6.3 Hz, 6H); $^{13}$C-NMR (75 MHz, CDCl$_3$) ppm δ 152.76, 146.87, 131.51, 111.79, 111.64, 107.57, 55.81, 53.89, 48.95, 48.77, 45.41, 28.75, 27.91, 22.56; MS (ES$^+$) m/z 249.2 (MH+).

1-(3-(Isopropylamino)propyl)indolin-7-ol, (11g). To a methanolic solution of a 9g (1 eq), was added 10% Pd/C. The mixture was stirred under H$_2$ at 4 atm. (Rubino et al., 2011), pressure for 23 h at room temperature in the presence of traces of acetone in the Parr hydrogenator. The mixture was then filtered through celite and concentrated to give comound 11g as a brown oil, in ~90% yield, and was used without further purification.

$^{1}$H-NMR (300 MHz, CDCl$_3$) ppm δ 6.70-6.56 (m, 3H), 3.36-3.30 (m, 4H), 2.98 (t, J=8.4 Hz, 2H), 2.85 (t, J=5.7 Hz, 2H), 2.83 (septet, J=6.6 Hz, 1H), 1.67 (quint, J=5.7 Hz, 2H), 1.10 (d. J=6.6 Hz, 6H); $^{13}$C-NMR (100 MHz, CDCl$_3$)ppm δ 144.11, 141.06, 131.46, 120.01, 117.38, 115.74, 54.53, 49.04, 48.80, 42.86, 29.61, 27.59, 21.77.

3-(Indolin-1-yl)-N-isopropylpropan-1-amine di-p-Toluenesulfonate (12a AN1284). Compound 12a was prepared by addition of p-TSA to a solution of 11a in t-butyl methyl ether. The ethereal solution was evaporated to give 18a as an hygroscopic brown solid, in 23% yield. $^{1}$H-NMR (300 MHz, CD$_3$OD) ppm δ 7.78 (d, J=8.1 Hz, 5H), 7.69-7.66 (m, 1H), 7.59-7.51 (m, 3H), 7.31 (d, J=7.8 Hz, 5H), 4.06 (t, J=7.5 Hz, 2H), 3.76 ("t", J=8.1 Hz, 2H), 3.47-3.36 (m, 3H), 3.26 (t, J=7.8 Hz, 2H), 2.45 (s, 8H), 2.33 (quint, J=7.8 Hz, 2H) 1.40 (d, J=6.6 Hz, 6H); $^{13}$C-NMR (75 MHz, CD$_3$OD) ppm δ 143.30, 141.86, 141.14, 136.47, 131.64, 129.85, 127.57, 126.85, 119.93, 55.30, 54.42, 52.28, 42.96, 28.93, 27.19, 23.14, 21.31, 19.19.

N-Isopropyl-3-(5-methoxyindolin-1-yl)propan-1-amine di-Hydrochloride, (12b AN1298). Compound 12b obtained by addition of a solution of HCl (gas)/ether to 11b, was isolated as a hygroscopic yellow solid in approximately quantitative yield. $^{1}$H-NMR (300 MHz, CDCl$_3$) ppm δ 7.08-7.05 (m, 1H), 6.91-6.90 (m, 1H), 6.85-6.82 (m, 1H), 3.77 (s, 3H), 3.67 (t, J=7.8, 2H), 3.42-3.34 (m, 3H), 3.19-3.11 (m, 4H), 2.12 (quint, J=7.5 Hz, 2H), 1.35 (d, J=6.6 Hz, 6H); $^{13}$C-NMR (75 MHz, CDCl$_3$) ppm δ 159.54, 139.55, 136.10, 116.08, 114.58, 112.34, 56.41, 55.43, 52.41, 52.08, 43.53, 29.41, 24.07, 19.25; MS (ES+) m/z 249.2 (MH$^+$).

1-(3-(Isopropylamino)propyl)indolin-7-ol di-p-Toluenesulfonate, (12g AN1280). Compound 12g was prepared by addition of p-TSA (0.39 g, 2 mmol) to 11g (0.2 g, 1 mmol) in t-butyl methyl ether (10 mL). The precipitate was crystallised from DCM-ether as a hygroscopic pink solid, and was isolated in quantitative yield. $^{1}$H-NMR (700 MHz, CD$_3$OD+D$_2$O) ppm δ 7.69 (d, J=8.4 Hz, 4H, H-20), 7.32 (t, J=7.7 Hz, 1H), 7.25 (d, J=8.4 Hz, 4H), 6.94 (dd, J=7.7, 0.7 Hz, 1H), 6.91 (d, J=7.7 Hz, 1H), 3.95 (t, J=7.7 Hz, 2H), 3.66 ("t", J=7.7 Hz, 2H), 3.37 (septet, J=6.3 Hz, 1H), 3.34 (t, J=7.7 Hz, 2H), 3.13 (t, J=7.7 Hz, 2H), 2.37 (s, 6H), 2.16 (quin, J=7.7 Hz, 2H), 1.33 (d, J=6.3 Hz, 6H); $^{13}$C-NMR (176 MHz, CD$_3$OD+D$_2$O) ppm δ 149.98, 142.95, 141.99, 138.18, 132.90, 129.92, 127.00, 126.82, 117.74, 116.41, 55.22, 53.35, 52.19, 43.02, 29.31, 23.06, 21.34, 19.20.

3-(1H-indol-1-yl)-N-isopropylpropanamide, (13a). Compound 13a synthesised from indole by Procedure D, was isolated as an orange oil in 59% yield. $^{1}$H-NMR (300 MHz, CDCl$_3$) ppm δ 7.61 (d, J=7.8 Hz, 1H), 7.36-7.33 (m, 1H), 7.20 (td, J=7.8, 0.9 Hz, 1H), 7.13-7.06 (m, 2H), 6.46 (d, J=2.7 Hz, 1H), 5.06 (bs, 1H), 4.46 (t, J=6.6 Hz, 2H), 3.95 (septet, J=6.6 Hz, 1H), 2.54 (t, J=6.6 Hz, 2H), 0.96 (d, J=6.6 Hz, 6H); $^{13}$C-NMR (75 MHz, CDCl$_3$) ppm δ 169.44, 135.66, 128.83, 128.28, 121.66, 121.15, 119.55, 109.30, 101.56, 42.71, 41.59, 37.72, 22.53; MS (ES$^+$) m/z 253 (MNa)$^+$ N-Isopropyl-3-(5-methoxy-1H-indol-1-yl)propanamide, (13b). Compound 13b synthesised from 5-methoxyindoline by Procedure D, was isolated as an orange solid in 85% yield, mp 68-71° C. $^1$H-NMR (300 MHz, CDCl$_3$) ppm δ 7.17 (d, J=8.7 Hz, 1H), 7.04-7.00 (m, 2H), 6.82 (dd, J=8.7, 2.4 Hz, 1H), 6.35 (d, J=3 Hz, 1H), 5.73-5.70 (m, 1H), 4.33 (t, J=6.3 Hz, 2H), 3.89 (septet, J=6.6 Hz, 1H), 3.62 (s, 3H), 2.49 (t, J=6.3 Hz, 2H), 0.93 (d, J=6.6 Hz, 6H); $^{13}$C-NMR (75 MHz, CDCl$_3$) ppm δ 170.10, 153.95, 130.88, 129.01, 128.55, 111.79, 109.92, 102.69, 101.04, 55.75, 42.68, 41.60, 37.43, 22.16; MS (ES$^+$) m/z 261 (MH+), 283 (MNa)$^+$, 299 (MK)$^+$ 3-(5-Chloro-1H-indol-1-yl)-N-isopropylpropanamide, (13d). Compound 13d synthesised from 5-chloroindole by Procedure D, was isolated bright orange solid, in approximately quantitative yield, mp 122-125° C. $^1$H-NMR (300 MHz, CDCl$_3$) ppm δ 7.51 (s, 1H), 7.22-7.18 (m, 1H), 7.10-7.05 (m, 2H), 6.35-6.34 (m, 1H), 4.33 (t, J=6.6 Hz, 2H), 3.90 (septet, J=6.6 Hz, 1H), 2.46 (t, J=6.6 Hz, 2H), 0.94 (d. J=6.6 Hz, 6H); $^{13}$C-NMR (75 MHz, CDCl$_3$) ppm δ 169.00, 133.91, 129.49, 129.36, 124.88, 121.53, 120.08, 110.20, 100.89, 42.53, 41.09, 37.06, 22.19; MS (ES$^+$) m/z 265 (MH$^+$), 287 (MNa)$^+$ 3-(6-Fluoro-1H-indol-1-yl)-N-isopropylpropanamide, (13e). Compound 13e synthesised from 6-fluoroindole by Procedure D, was isolated as a white solid, mp 86-87° C., in approximately quantitative yield. $^1$H-NMR (600 MHz, CDCl$_3$) ppm δ 7.50 (dd, J=9.0, 5.4 Hz, 1H), 7.08 (d, J=3.0 Hz, 1H), 7.03 (dd, J=9.6, 1.8 Hz, 1H), 6.86 (td, J=9.6, 2.4 Hz, 1H), 6.43 (d, J=3.0 Hz, 1H), 5.20-5.09 (m, 1H), 4.42 (t, J=6.6 Hz, 2H), 3.97 (septet, J=6.6 Hz, 1H), 3.69 (s, 3H), 2.55 (t, J=6.6 Hz, 2H), 0.98 (d, J=6.6 Hz, 6H); $^{13}$C-NMR (150 MHz, CDCl$_3$) ppm δ 169.20, 160.54+158.96, 135.65+135.57, 128.64+128.61, 125.10, 121.75+121.69, 108.28+108.11, 101.66, 95.78+95.61, 42.75, 41.60, 37.31, 22.42.

3-(Indolin-1-yl)-N-isopropylpropanamide, (14a). Compound 14a synthesised from 13a by Procedure B method III, was isolated as a yellow oil in 79% yield. $^1$H-NMR (400 MHz, CDCl$_3$) ppm δ 7.06-7.00 (m, 2H), 6.71-6.65 (m, 2H) 6.50 (d, J=7.6 Hz, 1H), 3.99 (septet, J=6.6 Hz, 1H), 3.33-3.20 (m, 4H), 2.90 (t, J=8.0 Hz, 2H), 2.41 (t, J=6.4 Hz, 2H), 1.08 (d, J=6.8 Hz, 6H); $^{13}$C-NMR (100 MHz, CDCl$_3$) ppm δ 171.32, 151.47, 130.11, 127.21, 124.47, 118.48, 107.47, 53.09, 46.15, 41.22, 34.01, 28.38, 22.19; MS (ES$^+$) m/z 233 (MH+), 255 (MNa)$^+$ 3-(5-Chloro-1H-indol-1-yl)-N-isopropylpropanamide, (14d). Compound 14d synthesised from 13d by Procedure B method III, was isolated as an orange oil, in 93% yield. $^1$H-NMR (300 MHz, CDCl$_3$) ppm δ 6.97-6.93 (m, 2H), 6.50-6.47 (m, 1H), 6.36 (d, J=8.1 Hz, 1H), 4.00 (septet, J=6.6 Hz, 1H), 3.32 (t, J=7.5 Hz, 4H), 2.88 (t, J=8.1 Hz, 2H), 2.40 (t, J=6.9 Hz, 2H), 1.10 (d, J=6.6 Hz, 6H); $^{13}$C-NMR (75 MHz, CDCl$_3$) ppm δ 170.76, 150.48, 131.82, 126.80, 124.53, 122.21, 107.54, 53.14, 45.69, 41.22, 34.08, 28.22, 22.39; MS (ES$^+$) m/z 267 (MH+), 289 (MNa)$^+$ 3-(6-Fluoroindolin-1-yl)-N-isopropylpropanamide, (14e). Compound 14e synthesised from 13e by Procedure B method III, was isolated as a white solid after sublimation, in 5% yield, mp 69-70° C. $^1$H-NMR (300 MHz, Acetone-d) ppm δ 6.93-6.90 (m, 1H), 6.25-6.18 (m, 2H), 3.96 (septet, J=6.6 Hz, 1H), 3.43 (t, J=8.4 Hz, 2H), 3.38 (t, J=6.9 Hz, 2H), 2.85 (t, J=8.4 Hz, 2H), 2.38 (t, J=6.9 Hz, 2H), 1.08 (d, J=6.6 Hz, 6H); $^{13}$C-NMR (75 MHz, Acetone-d6) ppm δ 170.56, 165.98, 162.83, 154.93+154.91, 126.13, 125.33+125.19,

51

103.09+102.79, 95.34+94.97, 54.07, 41.62+41.51, 34.49+
34.45, 28.29, 22.79; MS (ES⁺) m/z 251 (MH+), 273 (MNa)⁺

3-(Indolin-1-yl)-N-isopropylpropanamide Hydrochloride,
(15a AN1292). Compound 15a was prepared by addition of
3N HCl to 14a in ethyl acetate and was evaporated. The
precipitate was crystalized and was isolated as a white-
brown solid, mp 92-93° C., in approximately quantitative
yield. ¹H-NMR (300 MHz, CD₃OD) ppm δ 7.64 (d, J=7.2
Hz, 1H), 7.53-7.46 (m, 3H), 4.06 (t, J=7.2 Hz, 2H), 3.89
(septet, J=6.6 Hz, 1H), 3.87 (t, J=6.9 Hz, 2H), 3.39 (t, J=6.9
Hz, 2H), 2.87 (t, J=6.6 Hz, 2H), 1.14 (d, J=6.6 Hz, 6H);
¹³C-NMR (75 MHz, CD₃OD) ppm δ 169.96, 140.59,
136.64, 131.70, 129.66, 127.47, 120.18, 54.96, 53.65, 42.72,
31.22, 28.91, 22.44; MS (ES⁺) m/z 233 (MH+), 255 (MNa)⁺

3-(5-Chloro-1H-indol-1-yl)-N-isopropylpropanamide
Hydrochloride, (15d AN1287). Compound 15d was pre-
pared by addition of 3N HCl to 14d in EtOAc and was
evaporated. The precipitate was isolated as a dark yellow oil
in approximately quantitative yield. ¹H-NMR (300 MHz,
CD₃OD) ppm δ 7.66-7.63 (m, 1H), 7.56-7.50 (m, 2H), 4.08
(t, J=7.5 Hz, 2H), 3.90 (septet, J=6.6 Hz, 1H), 3.86 (t, J=6.9
Hz, 2H), 3.41 (t, J=7.5 Hz, 2H), 2.83 (t, J=6.9 Hz, 2H), 1.14
(d, J=6.6 Hz, 6H); ¹³C-NMR (75 MHz, CD₃OD) ppm δ
170.14, 139.73, 139.25, 137.35, 129.91, 127.685, 121.73,
55.57, 53.94, 42.82, 31.22, 29.03, 22.50; MS (ES⁺) m/z 267
(MH+), 289 (MNa)⁺

3-(6-Fluoroindolin-1-yl)-N-isopropylpropanamide
Hydrochloride, (15e AN1294). Compound 15e obtained by
addition of a solution of HCl (gas)/ether to 14e was isolated
as a hygroscopic white-pink solid, in approximately quan-
titative yield. ¹H-NMR (400 MHz, CD₃OD) ppm δ 7.52 (dd,

52

J=8.4, 5.4 Hz, 1H), 7.46 (dd, J=8.4, 2.0 Hz, 1H), 7.26 (td,
J=8.8, 2.4 Hz, 1H), 4.06 (t, J=7.6 Hz, 2H), 3.98 (septet,
J=6.4 Hz, 1H), 3.84 (t, J=6.8 Hz, 2H), 3.33 (t, J=7.6 Hz, 2H),
2.78 (t, J=6.8 Hz, 2H), 1.15 (d, J=6.8 Hz, 6H); ¹³C-NMR
(100 MHz, CD₃OD) ppm δ 170.48, 165.03+162.58, 142.71,
132.56, 128.89+128.80, 118.66+118.44, 108.09+107.81,
56.24, 53.90, 42.85, 31.17, 28.49, 22.54; MS (ES⁺) m/z 251
(MH+), 273 (MNa)⁺

3-(1H-Indol-1-yl)-N-isopropylpropan-1-amine, (16a).
Compound 16a prepared from 13a by Procedure F, was
isolated as a brown oil in 50% yield. ¹H-NMR (300 MHz,
CDCl₃) ppm δ 7.61-7.59 (m, 1H), 7.33-7.31 (m, 1H),
7.19-7.14 (m, 1H), 7.09-7.05 (m, 2H), 6.46 (d, J=3.3 Hz,
1H), 4.13 (t, J=6.9 Hz, 2H), 2.68 (septet, J=6.3 Hz, 1H), 2.52
(t, J=6.9 Hz, 2H), 1.93 (quint, J=6.9 Hz, 2H), 0.99 (d, J=6.3
Hz, 6H); ¹³C-NMR (75 MHz, CDCl₃) ppm δ 135.86,
128.50, 127.76, 121.29, 120.83, 119.16, 109.32, 100.97,
48.77, 44.35, 44.11, 41.05, 30.61, 22.65. MS (ES⁺) m/z
217.2 (MH+), 253 (MNa)⁺

N-Isopropyl-3-(5-methoxy-1H-indol-1-yl)propan-1-
amine, (16b). Compound 16b synthesised from 13b by
Procedure F, was isolated as a yellow oil in 50% yield.
¹H-NMR (300 MHz, CDCl₃) ppm δ 7.17 (d, J=9 Hz, 1H),
7.00 (d, J=15.3 Hz, 1H), 6.82 (dd, J=9, 2.1 Hz, 1H), 6.34 (d,
2.4 Hz, 1H), 4.04 (t, J=6.9 Hz, 2H), 3.75 (s, 3H), 2.62
(septet, J=6.2 Hz, 1H), 1.83 (quint, J=6.7 Hz, 2H), 0.96 (d,
J=6.6 Hz, 6H); ¹³C-NMR (75 MHz, CDCl₃) ppm δ 155.50,
130.91, 128.49, 127.90, 111.23, 109.72, 101.98, 100.08,
55.14, 48.27, 44.01, 43.79, 30.55, 22.56; MS (ES⁺) m/z
247.1 (MH+).

3-(1H-Indol-3-yl)propanamide, (17). To a solution of 3-indole propionic acid (IPA) (1 g, 4.93 mmol) in THF (15 mL) was added carbonyldiimidazole (1.1 g, 5.9 mmol) at room temperature. After stirring for 45 min, a solution of 30% NH$_4$OH (15 mL). The resulting reaction mixture was stirred for 16 h and was then evaporated. The residue was dissolved in DCM and washed with water and saturated aqueous NaCl. The organic layer was dried over Na$_2$SO$_4$ and evaporated. Compound 19 was isolated as a white solid, mp 125-127, in 70% yield. $^1$H-NMR (300 MHz, CDCl$_3$) ppm δ 9.99 (bs, 1H), 7.59-7.56 (m, 1H), 7.37-7.35 (m, 1H), 7.13-6.68 (m, 3H), 6.79 (bs, 1H), 6.17 (bs, 1H), 3.04 (t, J=7.5 Hz, 2H), 2.87 (bs, 1H), 2.56 (t, J=7.5 Hz, 2H); $^{13}$C-NMR (75 MHz, CDCl$_3$) ppm δ 175.00, 137.74, 128.43, 122.81, 122.01, 119.29, 115.61, 112.00, 37.06, 21.88.

3-(1H-Indol-3-yl)propan-1-amine, (18). Compound 18 was synthesised from 17 by Procedure F, to give 18 as a yellow oil, in approximately quantitative yield. $^1$H-NMR (300 MHz, CDCl$_3$) ppm δ 9.35 (bs, 1H), 7.52-7.50 (m, 1H), 7.22-7.19 (m, 1H), 7.12-7.01 (m, 2H), 6.74 (s, 1H), 2.77 (bs, 2H), 2.64 (t, J=7.2 Hz, 2H), 2.56 (t, J=7.2 Hz, 2H), 1.69 (quint, J=7.2 Hz, 2H); $^{13}$C-NMR (75 MHz, CDCl$_3$) ppm δ 136.27, 127.11, 121.43, 121.16, 118.40, 118.38, 114.86, 111.08, 61.45, 41.40, 33.36, 29.61, 22.14, 13.86.

3-(Indolin-3-yl)propan-1-amine, (19). Compound 19 was synthesised from 18 by Procedure B Method II, and was purified by elution through a short silica gel column with EtOAc-hexane (1:4), and was isolated as a yellow oil in 6% yield. $^1$H-NMR (300 MHz, CDCl$_3$) ppm δ 7.05-7.03 (m, 2H), 6.70 (t, J=7.5 Hz, 1H), 6.60 (d, J=7.8Hz, 1H), 6.74 (s, 1H), 2.77 (bs, 2H), 2.64 (t, J=7.2 Hz, 2H), 2.56 (t, J=7.2 Hz, 2H), 1.69 (quint, J=7.2 Hz, 2H); $^{13}$C-NMR (75 MHz, CDCl$_3$) ppm δ 136.27, 127.11, 121.43, 121.16, 118.40, 118.38, 114.86, 111.08, 61.45, 41.40, 33.36, 29.61, 22.14, 13.86.

3-(Indolin-3-yl)propan-1-amine di-p-Toluenesulfonate, (20 AN1282). Compound 20 was prepared by addition of p-TSA to a solution of 19 in t-butyl methyl ether. The ethereal solution was evaporated to give 20 as a red-brown oil, in approximately quantitative yield. $^1$H-NMR (300 MHz, CDCl$_3$) ppm δ 7.05-7.03 (m, 2H), 6.70 (t, J=7.5 Hz, 1H), 6.60 (d, J=7.8Hz, 1H), 6.74 (s, 1H), 2.77 (bs, 2H), 2.64 (t, J=7.2 Hz, 2H), 2.56 (t, J=7.2 Hz, 2H), 1.69 (quint, J=7.2 Hz, 2H); $^{13}$C-NMR (75 MHz, CDCl$_3$) ppm δ 136.27, 127.11, 121.43, 121.16, 118.40, 118.38, 114.86, 111.08, 61.45, 41.40, 33.36, 29.61, 22.14, 13.86.

Measurement of Protective Activity Against Oxidative Stress in a Macrophage Cell Culture Compounds of the invention were tested for their potential to protect against cell death induced by oxidative stress in a mouse macrophage (RAW 264.7) cell line. Cells were cultured in Dulbecco's Modified Eagle's Medium (DMEM), 4500 mg/L D-glucose with 10% foetal calf serum (FCS), 10000 U/mL penicillin, 100 mg/mL streptomycin and 25 μg/mL Amphotericin B at 37° C. with 95% air and 5% CO$_2$. Cells were seeded in 96 well-plates at a density of 1×10$^4$ cells/well and incubated with different compounds of the invention in several concentrations ranging from 10$^{-14}$-10$^{-9}$ M, for 2 h prior to addition of H$_2$O$_2$ (150 μM). Cell viability was measured 24 h later by means of the MTT (3-(4,5-dimethyl thiazol-2-yl)-2,5,diphenyl tetrazolium bromide) assay. MTT measures the activity of mitochondrial dehydrogenase in viable cells and is based on the reduction of yellow MTT to dark blue formazan crystals by mitochondrial dehydrogenases (succinate dehydrogenase). MTT solution was added to each well in a final concentration of 0.5 mg/ml. After 2 h, the MTT containing medium was aspired. Cells were lysed with 3% SDS and formazan crystals were dissolved in isopropanol/HCl. Optical density was determined by means of a plate-reader at a wavelength of 570 nm. Cell viability was reduced by H$_2$O$_2$ by 25-35% relative to that in control cells.

Measurement of Caspase 3 Activity in RAW Macrophage 264.7 Cells

Oxidative stress can cause apoptosis, a form of cell suicide mediated by a cascade of proteolytic enzymes called caspases (cysteinyl aspartate-specific proteases). Caspase 3 is one of a number of effector caspases. Its activity was measured by means of a luminescent assay (Caspase-Glo 3/7 Assay Promega Ltd). Macrophages were pre-treated as described above with concentrations of 10$^{-12}$ and 10$^{-9}$ M of several of the compounds 4 h before the addition of H$_2$O$_2$ (100 μM). The medium was aspirated 90 min later, 100 μL of DMEM was added to each well and the plates kept in an incubator overnight. Caspase-GloR Reagent (100 μL) was added to each well and the contents gently mixed using a plate shaker at 300-500 rpm for 30 sec. The plates were left at room temperature for 30 min and then luminescence of each sample was measured in a plate-reading luminometer (Cytation 3).

Measurement of Anti-Inflammatory Activity in a Mouse Macrophage Cell Line Culture Anti-inflammatory activity was measured in RAW 264.7 macrophage cells. The cells were seeded at density of $5\times10^4$ per well in 48-well culture plates and grown overnight in DMEM as described above. The compounds were added to give final concentrations ranging from $1\times10^{-12}$-$1\times10^{-6}$ M of the respective salts per well. The cells were incubated for 2 h at 37° C. prior to stimulation with lipopolysaccharide (LPS, 2.5 µg/mL) from Escherichia coli (Sigma-Aldrich). Supernatants were harvested after 8 h for detection of TNF-α and after 24 h for nitric oxide (NO). NO production was detected by a colourimetric method using Griess reagent (0.2% naphthylenediamine dihydrochloride, and 2% sulfanilamide in 5% phosphoric acid), which measures the concentration of nitrite, a stable metabolite produced from NO. TNF-α protein was detected by means of the sandwich ELISA method using an ELISA kit (Biolegend, San Diego, CA, USA) according to the manufacturer's instructions.

Measurement of Anti-Inflammatory Activity in Human Honocytes and Macrophages

Blood (20 ml was collected from healthy human subjects on the day of the experiment in anti-coagulant tubes and diluted in PBS 1:1. Ficol (12 mL) was added into the bottom of the tube, centrifuged slowly for 30 min at 1400 g and peripheral blood mononuclear cells (PBMCs) were separated. Monocytes were isolated by addition of 15 ml of MACS buffer. After centrifugation at 1400 g for 10 min at 4° C., the supernatant fluid was removed, monocytes were isolated by means of a MACS-Monocyte isolation kit (cat: 130-091-153) and incubated at 4-8° C. for 10 min Monocytes (500,000/well) were seeded in 12 multi well plate and cultured for 7 days in RPMI+L-Glutamin+FBS (10%) and PenStrep and h-MCSF (20 ng/mL) to convert them into macrophages. Compounds (AN1284, AN1297, AN1298, $1\times10^{-10}$ or $1\times10^{-9}$ M) were added 2 h before LPS (100 µg/mL Sigma Ltd. phenol extracted from Escherichia coli 055: B5) and incubated at 37° C., 5% $CO_2$. TNF-α, IL-1β and IL-6 protein were detected by means of the sandwich ELISA method using an ELISA kit for human cytokines (Biolegend, San Diego, CA, USA) according to the manufacturer's instructions.

Evaluation of Anti-Inflammatory Activity in Mice

Male Balb/c OlaHsd mice (aged 7-8 weeks) were injected subcutaneously (sc) with saline, or with AN1279, AN1283, AN1284, AN1287 and AN1298 at doses that contain approximately the equivalent amount of the base. LPS (10 mg/kg) was given by intraperitoneal injection 15 min later. The mice were sacrificed 4 h later, which was previously shown to be the optimal time for elevation of cytokines in the spleen and brain. The spleen, brain and liver were rapidly removed and frozen in liquid nitrogen and stored at −80° C. until use. A piece of the cortex was taken for gene analysis of cytokines. Blood was collected into heparinized tubes and plasma separated by centrifugation. For measurement of cytokine protein, tissues were weighed and diluted in PBS containing 0.8% NaCl, 0.144% $NaHPO_4$, 0.024% $KH_2PO_4$ and protease inhibitor cocktail (Sigma) and homogenised in an Ultra-TURRAX® homogeniser at a speed of 24,000 rpm and centrifuged at 14000 g for 15 min at 4° C. Cytokines were detected by means of Elisa kits (Biolegend) and protein concentration was determined by a bicinchoninic acid protein assay kit (Thermo Scientific, IL, USA).

For evaluation of cytokine mRNA, RNA was extracted from the tissue with Tri Reagent® (Sigma) and was reverse transcribed into cDNA by means of a high capacity cDNA reverse transcription kit (Applied Biosystems). For qRT- PCR, TaqMan Fast Universal PCR Master Mix (Applied Biosystems) and TaqMan Gene Expression Assays reagents (Applied Biosystems) were used. Hypoxanthine phosphoribosyl transferase (HPRT) was used as house-keeping gene and all results are normalised thereto.

Pharmacodynamic Assessment of Indoline Derivatives for Tuberous Sclerosis—

RERT/TSC1$^{f/f}$ mice develop kidney pathology that resembles human tuberous sclerosis (TSC). Mice bearing a floxed allele of TSC1 were purchased from Jackson laboratories and crossed to homozygosity to the RERT strain, provided by Dr. Mariano Barbacid, Spanish National Cancer Research Centre. The RERT strain contains an IRES-Cre-ERT2 knock in into the large subunit of RNA polymerase II, allowing an inducible deletion in all cell types by administration of tamoxifen. Mice were kept on the mixed background originally provided by Jackson and bred for over 20 generations to form a congenic colony of RERT/TSC1$^{f/f}$ mice with an undefined genetic background that shows an accelerated development of disease. The mice were injected sc with tamoxifen to induce TSC1 deletion and its effect assessed on body weight and immunological parameters associated with inflammation. AN1284 (1 µmole/kg of the 2HCl salt) was injected sc, twice daily in a group of 5 female mice 5 weeks after tamoxifen challenge. An untreated group of 5 tamoxifen challenged mice served as controls. The mice were weighed once weekly and observed for development of lethargy and eye closure.

Pharmacodynamic Assessment of Indoline Derivatives for Diabetic Nephropathy

The renal proximal tubule is uniquely susceptible to a variety of metabolic and hemodynamic factors associated with diabetes, predominantly to hyperglycaemia. Glucose entry into renal proximal tubular cells is insulin-independent, making these cells particularly sensitive to the deleterious effects of chronic hyperglycaemia in subjects with diabetes. To induce diabetic nephropathy, male 20, 8-week-old C57B1/6 mice were given five consecutive intraperitoneal injections of streptozotocin (STZ) (50 mg/kg per day). A control group of 10 mice was given 0.1 mol/L citrate buffer (pH 4.5). Ten days following the last injection of STZ, half the mice were treated twice daily with sc injections of AN1284 2HCl (2 µmoles/kg), or vehicle (saline) for fifteen weeks.

Pharmacodynamic Assessment of Indoline Derivatives for Acute Pancreatitis

The most commonly used animal model for acute pancreatitis is the cerulein-induced mouse model (Su et al., 2006). Cerulein is a cholecystokinin analogue that produces hyperstimulation of the pancreatic acinar cells at supramaximal dosage. The acute necrotizing pancreatitis produced is histopathologically similar to acute human pancreatitis (Van Acker et at, 2007).

Groups of 10 Balb/C male mice weighing 24 gm were injected intraperitoneally once every hour for 4 hours with cerulean (50 µg/kg) suspended in saline. AN1297 (1 or 2 mg/kg) or resolvin D (1 mg/kg) or saline that were injected sc. 30 min after the first cerulean injection. Mice were killed by exsanguination at 4 hours after the first cerulein injection. Blood samples or measurement of amylase were obtained by direct intracardiac puncture. Pancreases were removed immediately, flash frozen in liquid nitrogen and stored −80° C. until assayed, for TNF-α protein by means of the sandwich ELISA method using an ELISA kit (Biolegend, San Diego, CA, USA) according to the manufacturer's instructions. Serum amylase activity was determined using a colorimetric assay kit (ab102523, Abcam). The values of serum amylase activity are expressed as units per litre (U/l).

Results

Compounds AN1283, AN1284, AN1287, AN1292, AN1294, AN1295, AN1296, AN1297, AN1298, AN1299 and AN1400, were tested as HCl or 2HCl (AN1298) salts and the proportion of base in the total salt ranged from 0.78-0.88. Compounds AN1285, AN1279 and AN1293 were tosylate salts in which the proportion of base in the total salt ranged from 0.57-0.63. Compounds AN1264, AN1276, AN1282 were di-tosylate salts in which the proportion of base in the total salt ranged from 0.22-0.37.

Protection Activity of Compounds of the Invention Against Oxidative Stress in Cell Cultures Significant protection (increase in viability to level of controls without $H_2O_2$) was obtained over the concentration range of $1 \times 10^{-13}$-$1 \times 10^{-9}$ M by the following compounds; AN1264, AN1282, AN1284, AN1285, AN1287, AN1292, AN1297 and AN1299. AN1283, AN1276 and AN1279 caused this level of protection at concentrations of $1 \times 10^{-13}$-$1 \times 10^{-11}$ M and compounds AN647, AN1287 and AN1400, at concentrations of $1 \times 10^{-}$-$1 \times 10^{-9}$ M.

Reduction by Compounds in Elevation of Caspase 3 Induced in RAW Macrophages by $H_2O_2$ All the compounds tested at concentrations of $10^{-13}$ and $10^{-9}$ M significantly reduced caspase 3 activity in macrophages subjected to oxidative stress with $H_2O_2$ (FIG. 1). AN1264 and AN1279 ($1 \times 10^{-13}$M) caused less reduction in caspase 3 activity than the other compounds in keeping with their smaller degree of protection in the MTT assay.

Reduction by the Compounds of NO and Cytokines, TNF-$\alpha$ and IL-6 in LPS-Stimulated Macrophages The steroid budesonide was used as a positive control for these experiments. The range of concentrations with which a reduction of at least 25% in NO release from LPS-stimulated macrophages was obtained (ranging up to 50% at concentrations of 1 nM) is shown in Table 1. Compounds that caused a significant decrease at the lowest concentrations of $1 \times 10^{-12}$ or $1 \times 10^{-11}$ M were AN1283, AN1284 and AN1298. These compounds all have their side chains in position 1.

TABLE 1

Reduction by compounds of release
of NO from LPS-activated RAW cells

| Concentration range | Compounds (position of side chain) |
|---|---|
| $1 \times 10^{-12}$M-$1 \times 10^{-6}$M | AN1283 (1) |
| $1 \times 10^{-11}$M-$1 \times 10^{-6}$M | AN1284 (1) |
| $1 \times 10^{-10}$M-$1 \times 10^{-6}$M | Budesonide, AN647 (3) AN1264 (1) AN1292 (1) AN1298 (1) AN1299 (1) AN1400 (1) |
| $1 \times 10^{-10}$M-$1 \times 10^{-8}$M | AN1294 (1) AN1296 (1) AN1297 (1) |
| $1 \times 10^{-8}$M-$1 \times 10^{-6}$M | AN1276 (1) AN1280 (1) AN1282 (3) |
| $1 \times 10^{-8}$M-$1 \times 10^{-7}$M | AN1285 (1) AN1287 (1) |

Data represent range of concentrations over which budesonide and the indoline derivatives significantly reduced the release of NO from LPS activated RAW macrophages.

TABLE 2

Reduction by compounds of release of
TNF-$\alpha$ from LPS-activated RAW cells

| Concentration range | Compounds (position of side chain) |
|---|---|
| $1 \times 10^{-11}$M-$1 \times 10^{-6}$M | AN1283 (1) AN1284 (1) AN1298 (1) |
| $1 \times 10^{-10}$M-$1 \times 10^{-6}$M | Budesonide, AN647 (3) AN1264 (1) |

TABLE 2-continued

Reduction by compounds of release of
TNF-$\alpha$ from LPS-activated RAW cells

| Concentration range | Compounds (position of side chain) |
|---|---|
| $1 \times 10^{-10}$M-$1 \times 10^{-8}$M | AN1296 (1) |
| $1 \times 10^{-10}$M-$1 \times 10^{-7}$M | AN1294 (1) AN1297 (1) AN1299 (1) AN1400 (1) |
| $1 \times 10^{-9}$M-$1 \times 10^{-6}$M | AN1276 (1) AN1282 (1) |
| $1 \times 10^{-9}$M-$1 \times 10^{-7}$M | AN1285 (1) |
| $1 \times 10^{-8}$M-$1 \times 10^{-6}$M | AN1280 (1) AN1287 (1) |

Data represent range of concentrations over which budesonide and the indoline derivatives significantly reduced the release of TNF-$\alpha$ from LPS activated RAW macrophages.

They were also the most potent as inhibitors of the release of TNF-$\alpha$ (Table 2). When the propionic ester or propylamine side chain was in position 3 (AN647 and AN1282, respectively) the lowest concentration that inhibited NO and TNF-$\alpha$ release by 25% was $1 \times 10^{-10}$ M. Substitution of propylamine by N-isopropylpropylamine (AN1284) decreased by 10 fold the concentration that inhibited significantly the release of NO and TNF-$\alpha$. While introduction of $OCH_3$ in position 5 of AN1284 (AN1298) does not affect the activity of the compound, a 100-fold greater concentration of the amine with 5-Cl substituent (AN1285) was need to cause the same effect.

Anti-Inflammatory Activity of Compounds in Human Monocytes

The effect of AN1284, AN1297 and AN1298 on the release of TNF-$\alpha$ and IL-6 from human monocytes activated by LPS is shown in Table 1. TNF-$\alpha$ was measured 6, 12 and 24 h after addition of LPS in different subjects and that of IL-6 only after 24 h. All three compounds cause a similar, concentration-dependent statistically significant reduction in TNF-$\alpha$, which was greatest 24 h after addition of LPS. They also cause a similar reduction of IL-6 as shown in Table 3.

TABLE 3

Reduction by three indoline derivatives of TNF-$\alpha$
and IL-6 in human macrophages after their elevation by LPS.

| Time after LPS (h) | Cytokine | Concentration M | Reduction (%) ± STD compared to LPS alone Compounds | | |
|---|---|---|---|---|---|
| | | | AN1284 | AN1297 | AN1298 |
| 6 | TNF-$\alpha$ | $1 \times 10^{-9}$ | 55.3 ± 9.8 | 55.7 ± 11.5 | 50.4 ± 13.5 |
| 12 | | $1 \times 10^{-11}$ | 7.1 ± 5.8[#] | 22.0 ± 7.2 | 14.6 ± 4.2 |
| 12 | | $1 \times 10^{-10}$ | 41.1 ± 5.4 | 25.1 ± 10.9 | 28.0 ± 7.9 |
| 24 | | $1 \times 10^{-9}$ | 71.4 ± 9.7 | 71.1 ± 8.9 | 72.2 ± 9.7 |
| 24 | IL-6 | $1 \times 10^{-9}$ | 64.7 ± 14.8 | 62.4 ± 16.5 | 54.6 ± 18.8 |

All reductions except that marked by [#] are significant p < 0.05.

Figure 2A:
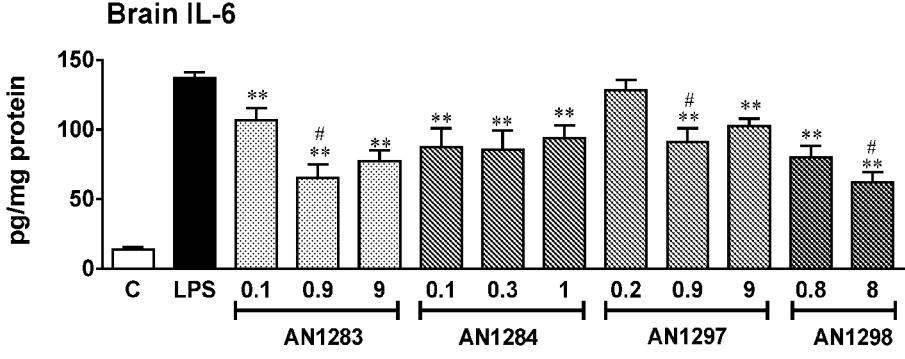
FIGS. 2A-2B shows the reduction by compounds of the levels of IL-6 in the brain (FIG. 2A) and liver (FIG. 2B) of LPS-injected mice. Data represent the mean and SEM from 6-12 mice per dose. Significantly different from LPS+saline *$p<0.05$; **$p<0.01$. Significantly different from preceding dose, # $p<0.05$.
Figure 2B:
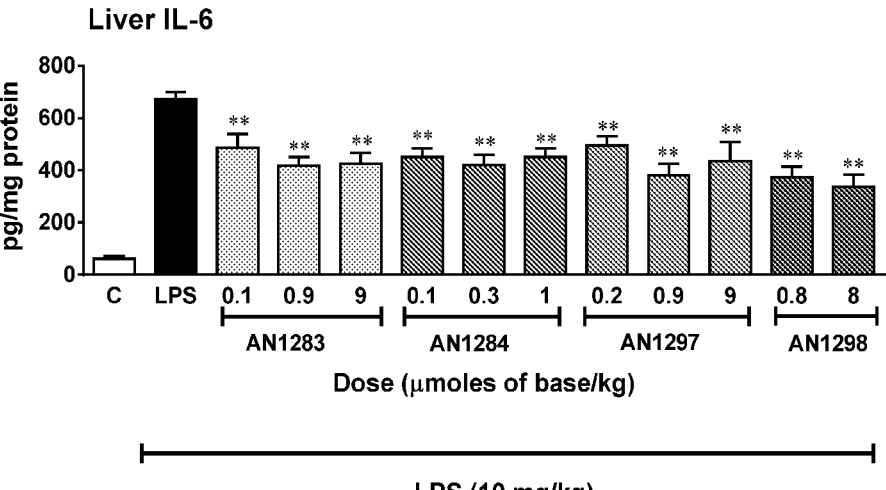
Figure 3A:
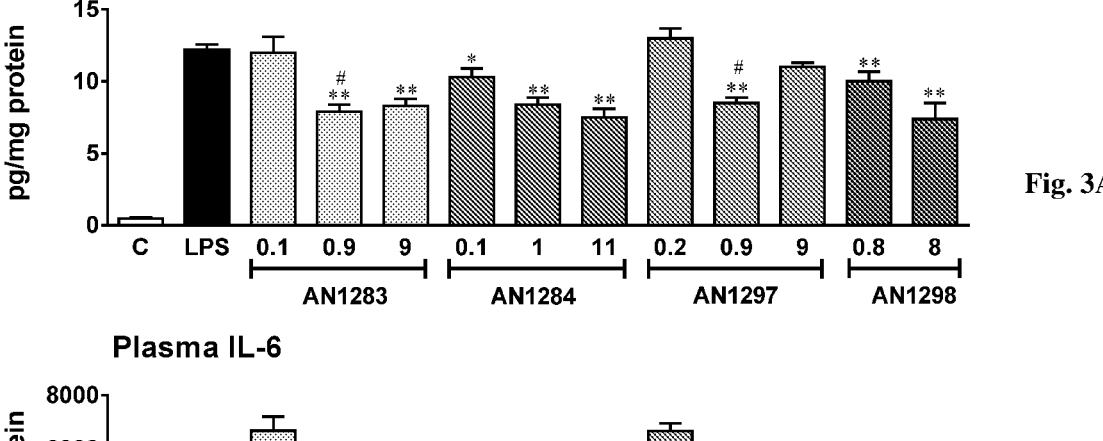
FIGS. 3A-3B shows the reduction by compounds of the levels of TNF-α (FIG. 3A) and IL-6 (FIG. 3B) in plasma of LPS-injected mice. Data represent the mean and SEM from 6-12 mice per dose. Significantly different from LPS+saline *$p<0.05$; **$p<0.01$. Significantly different from preceding dose, # $p<0.05$.
Figure 3B:
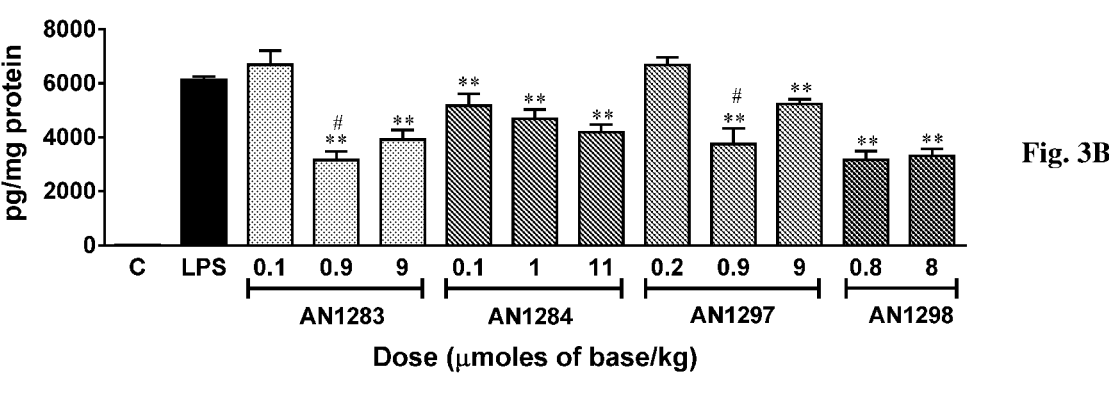
Figure 4A:
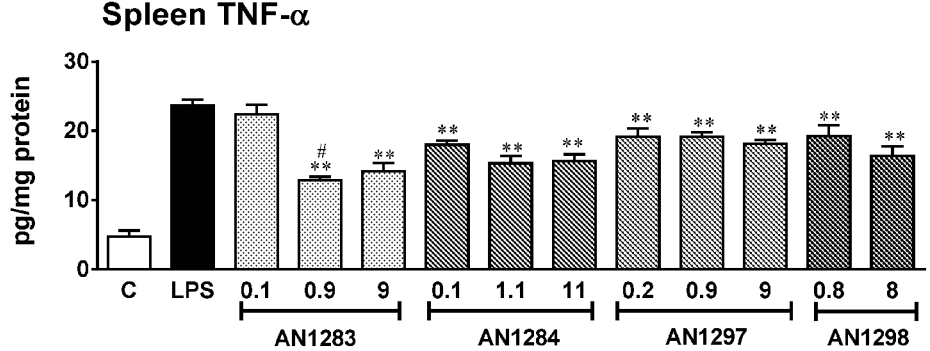
FIGS. 4A-4B shows the reduction by compounds of the levels of TNF-α (FIG. 4A) and IL-6 (FIG. 4B) in spleen of LPS-injected mice. Data represent the mean and SEM from 6-12 mice per dose. Significantly different from LPS+saline **$p<0.01$. Significantly different from preceding dose, # $p<0.05$.
Figure 4B:
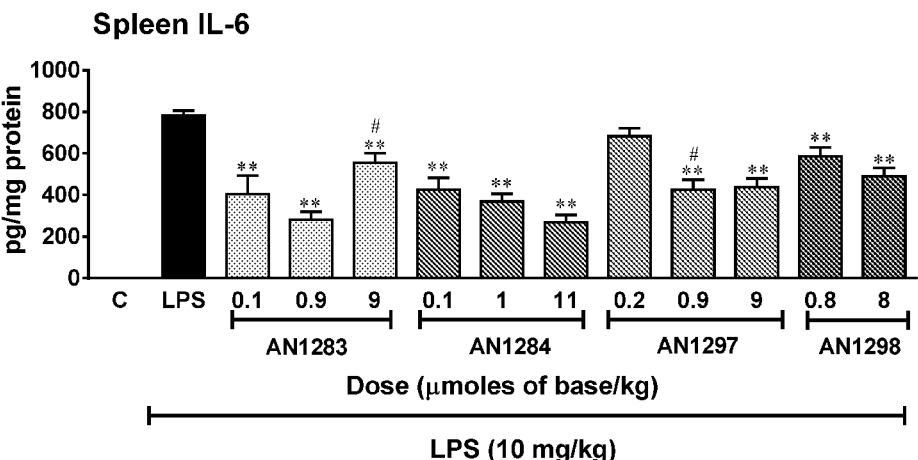

Reduction of Pro-Inflammatory Cytokine Proteins in Tissues of Mice Injected With LPS The only cytokine protein that increases consistently in the brain and liver to measurable amounts, 4 h after LPS injection was IL-6. FIG. 2 shows the reduction by 2-3 doses (expressed as the µmoles/kg of the base) of AN1283, AN1284, AN1297 and AN1298 of IL-6 in the brain and liver. Both IL-6 and TNF-$\alpha$ increased in plasma and spleen after LPS. The optimal time for elevation of these cytokines in plasma is 1.5-2 h. The reduction of these cytokines by different doses of four AN compounds is shown in FIGS. 3 and 4 respectively.

Reduction of Pro-Inflammatory Cytokine mRNAs in Brain of Mice Injected With LPS

Figure 5A:
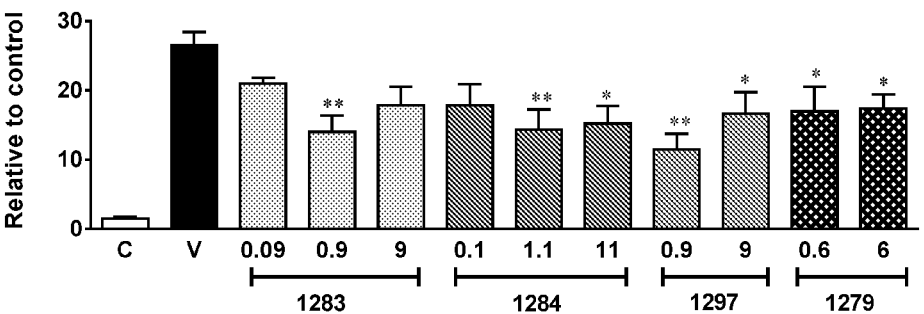
FIGS. 5A-5C shows the reduction by compounds of TNF-α (FIG. 5A), IL-1β (FIG. 5B) and IL12b (FIG. 5C) mRNA in the brain of LPS-injected mice. Data represent the mean and SEM from 6-12 mice for each group. Significantly different from LPS+saline *$p<0.05$; **$p<0.01$.
Figure 5B:
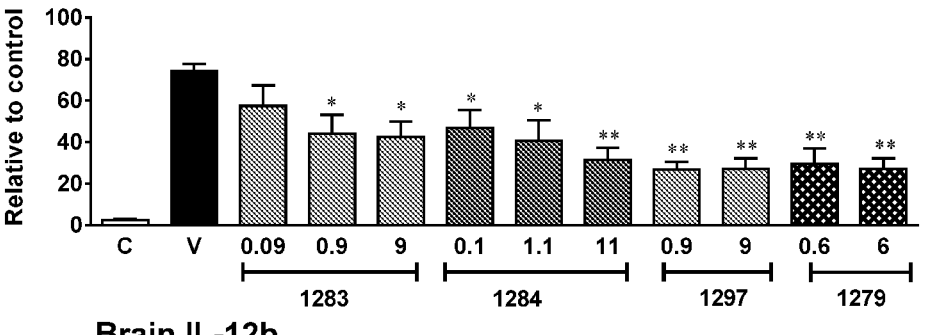
Figure 5C:
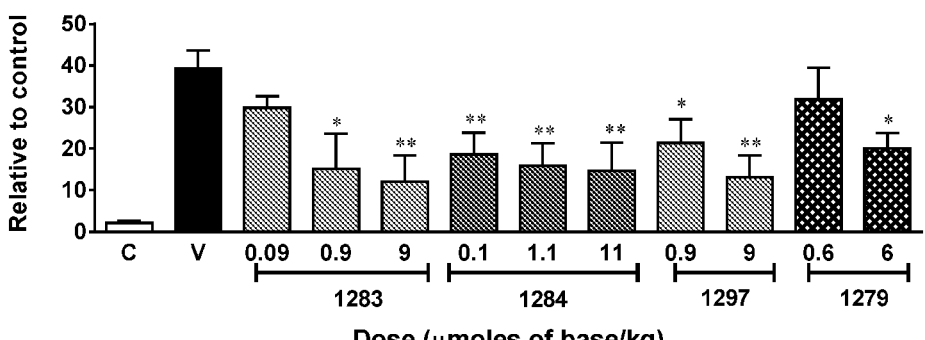

Four compounds also reduce the expression of pro-inflammatory genes, TNF-α, IL-β and IL-12b in the brain that are increased by injection of LPS (FIG. 5). This shows that the compounds are able to reach the CNS.

Reduction of Morbidity and Immune Parameters in TSC1-Deleted Mice

Figures 6A, 6B:
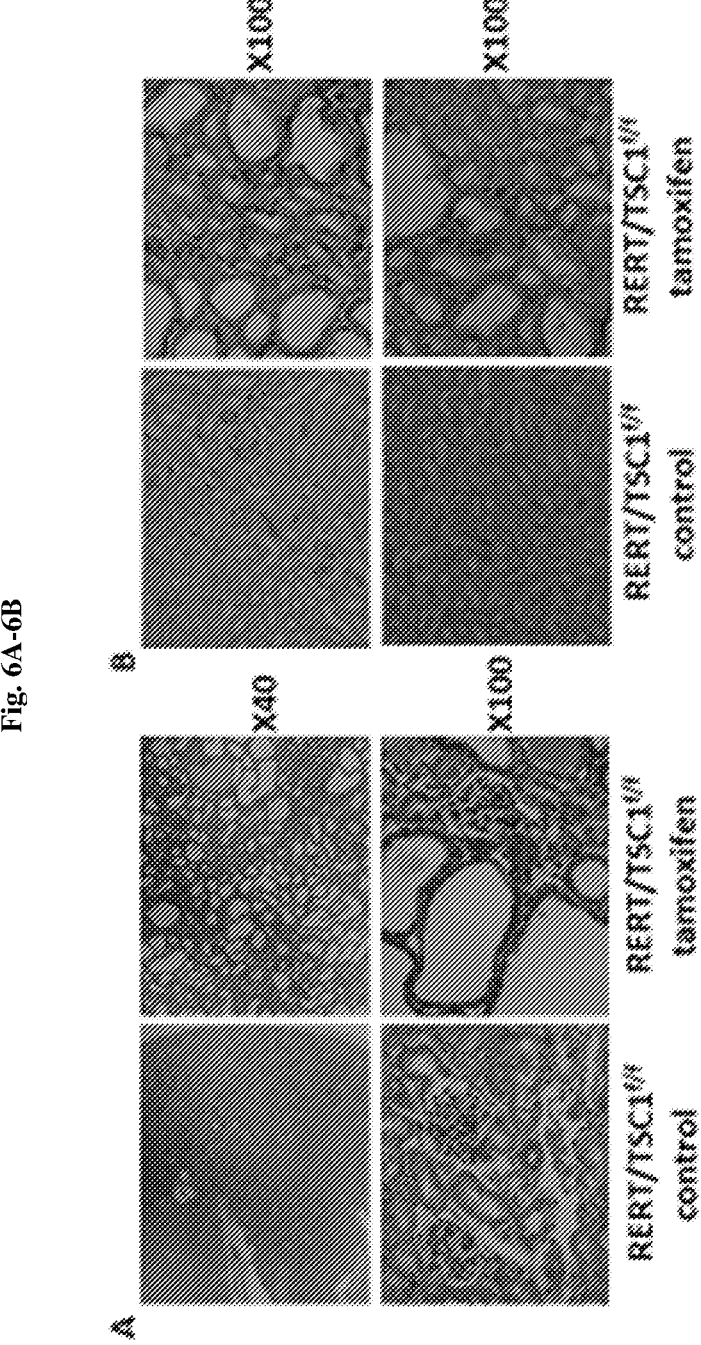
FIGS. 6A-6B shows the TSC1 deletion causes the development of renal cysts and increase in proliferation in situ. Typical histological appearances of the kidneys of mice stained with FIG. 6A. haematoxylin and eosin (H&E) FIG. 6B. immunohistochemistry for Ki67.

Signs of deteriorating health were observed within 8-10 weeks following tamoxifen challenge in the mice. This was manifested by reduction in body weight, lethargic behaviour and the appearance of eye exudates and seizures, a pathology associated with the human disease. Ten weeks from the time of tamoxifen injection, mice were sacrificed and analysed for gross pathology and markers of inflammation. The kidneys were enlarged with the development of large cysts (FIG. 6A) Staining with Ki67, a marker for proliferating cells revealed massive proliferation in the TSC1 KO mice indicative of development of a benign tumour or hyper-proliferation (hamartomas) that are typical for TSC (FIG. 6B).

Figure 7:
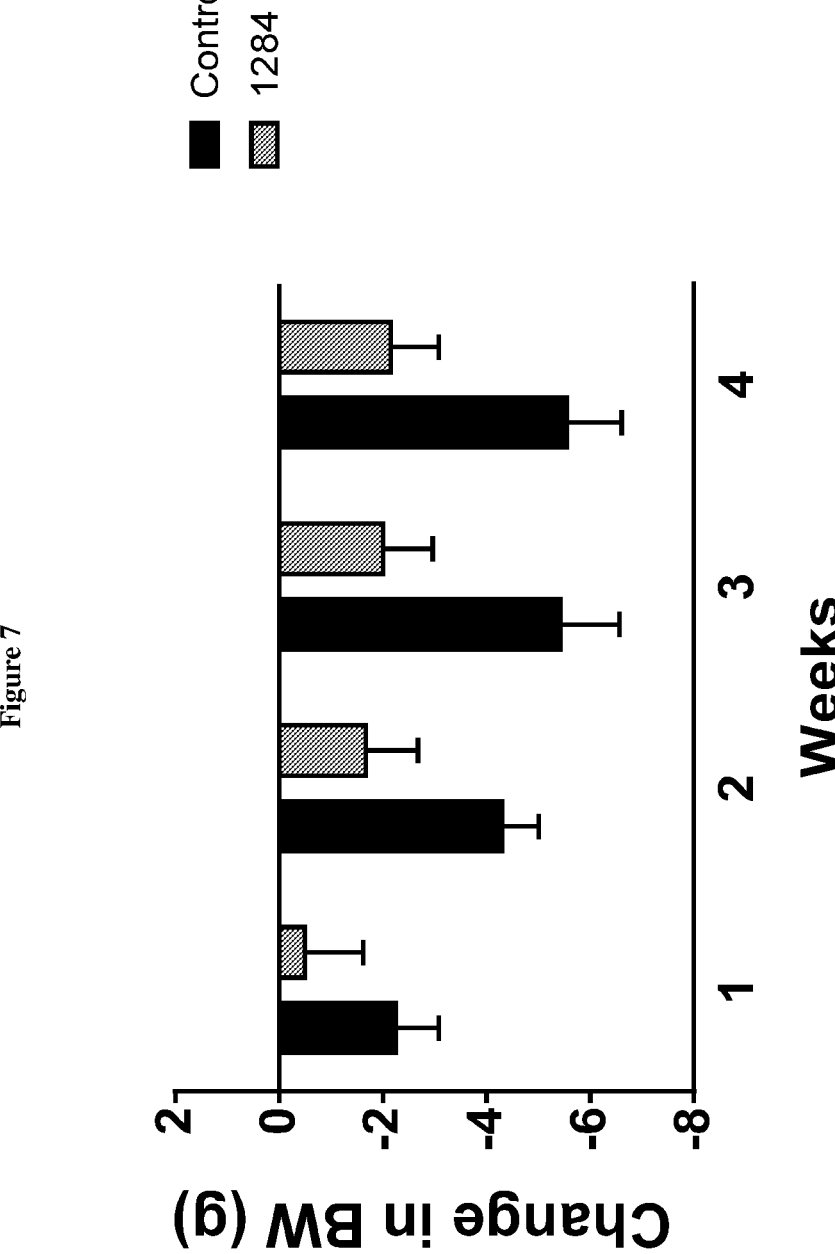
FIG. 7 shows how the AN1284 treatment improves the well-being of tamoxifen-induced RERT/TSC1$^{f/f}$ mice. AN1284-treated mice lost much less weight and were more active than the untreated controls.
Figure 8A:
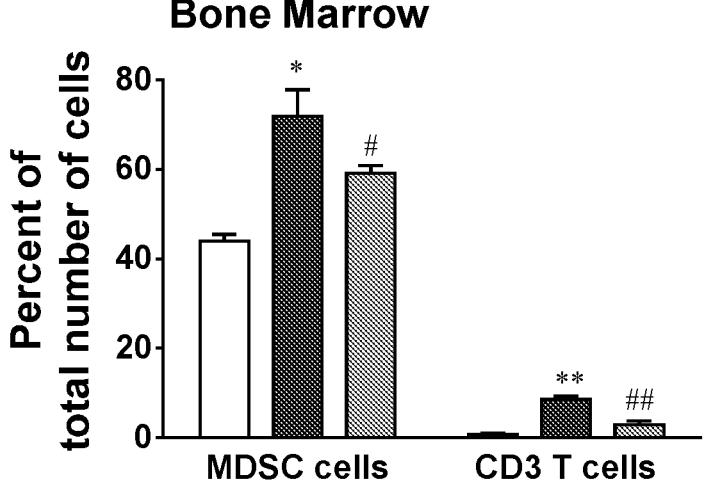
FIGS. 8A-8B shows how AN1284 treatment decreases the numbers of MDSC and T cells in the bone marrow (FIG. 8A) and spleen (FIG. 8B) of tamoxifen-induced RERT/TSC1$^{f/f}$ mice. Significantly different from control mice, *$p<0.05$, **$p<0.01$; significantly different from untreated RERT/TSC1$^{f/f}$ mice+tamoxifen, # $p<0.05$, ## $p<0.01$.
Figure 8B:
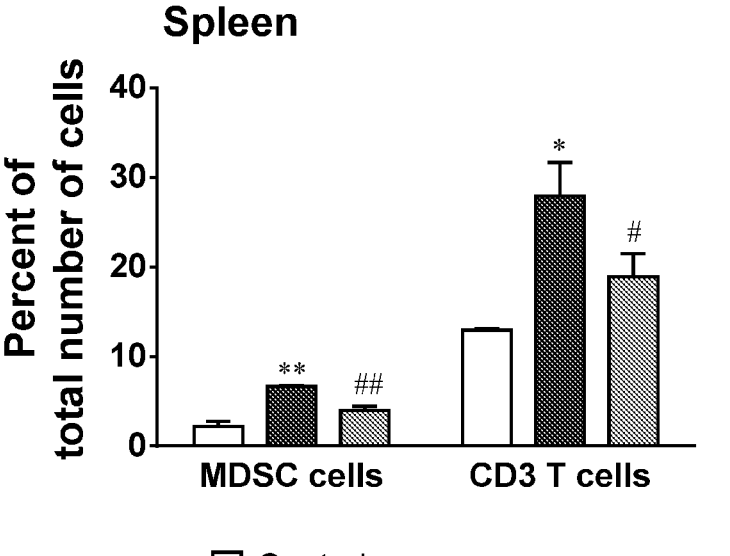
Figure 9A:
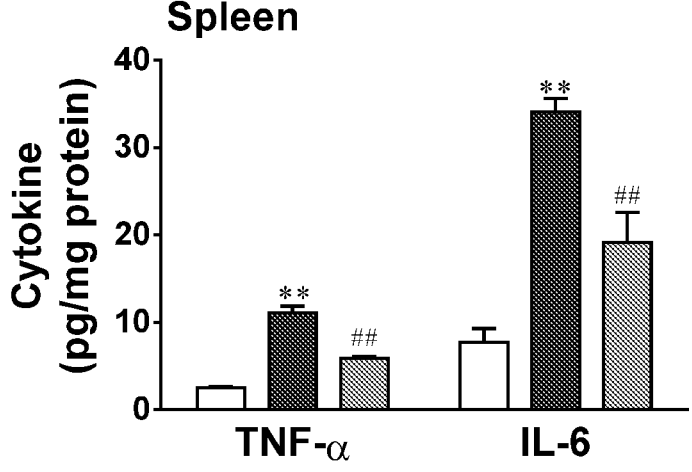
FIGS. 9A-9B shows how AN1284 decreases the elevation of cytokines TNF-α and IL-6 in spleen (FIG. 9A) and liver (FIG. 9B) of RERT/TSC1$^{f/f}$ mice+tamoxifen. Significantly different from control mice **. $p<0.01$, significantly different from untreated RERT/TSC1$^{f/f}$ mice+tamoxifen, ##$p<0.01$.
Figure 9B:
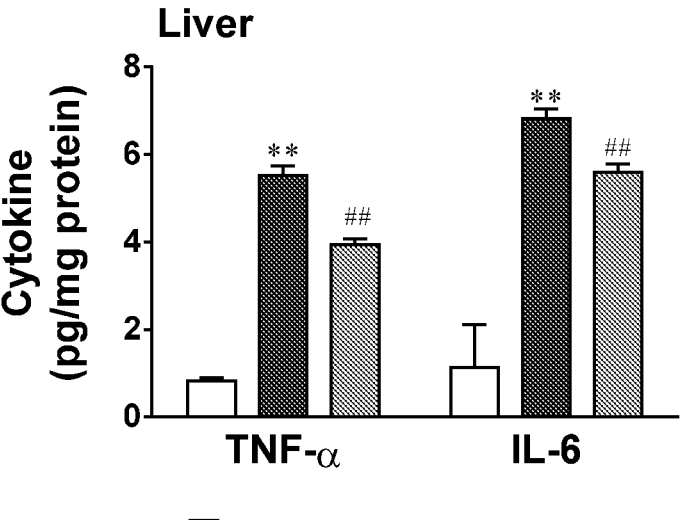

Five weeks after the initiation of AN1284 treatment the untreated group lost much weight and were so lethargic that they had to be terminated. Remarkably, none of the AN1284-treated mice developed severe lethargy and their body weight showed a much smaller decrease (FIG. 7). Flow cytometry analyses revealed a significant reduction in MDSCs in the bone marrow and spleen and in T cells in the bone marrow and spleen in the AN1284-treated mice (FIG. 8). A significant reduction was also shown for cytokine levels of TNF-α and IL-6 measurements in spleen and liver in the AN-1284 treated mice as compared with the untreated group (FIG. 9).

Figure 10:
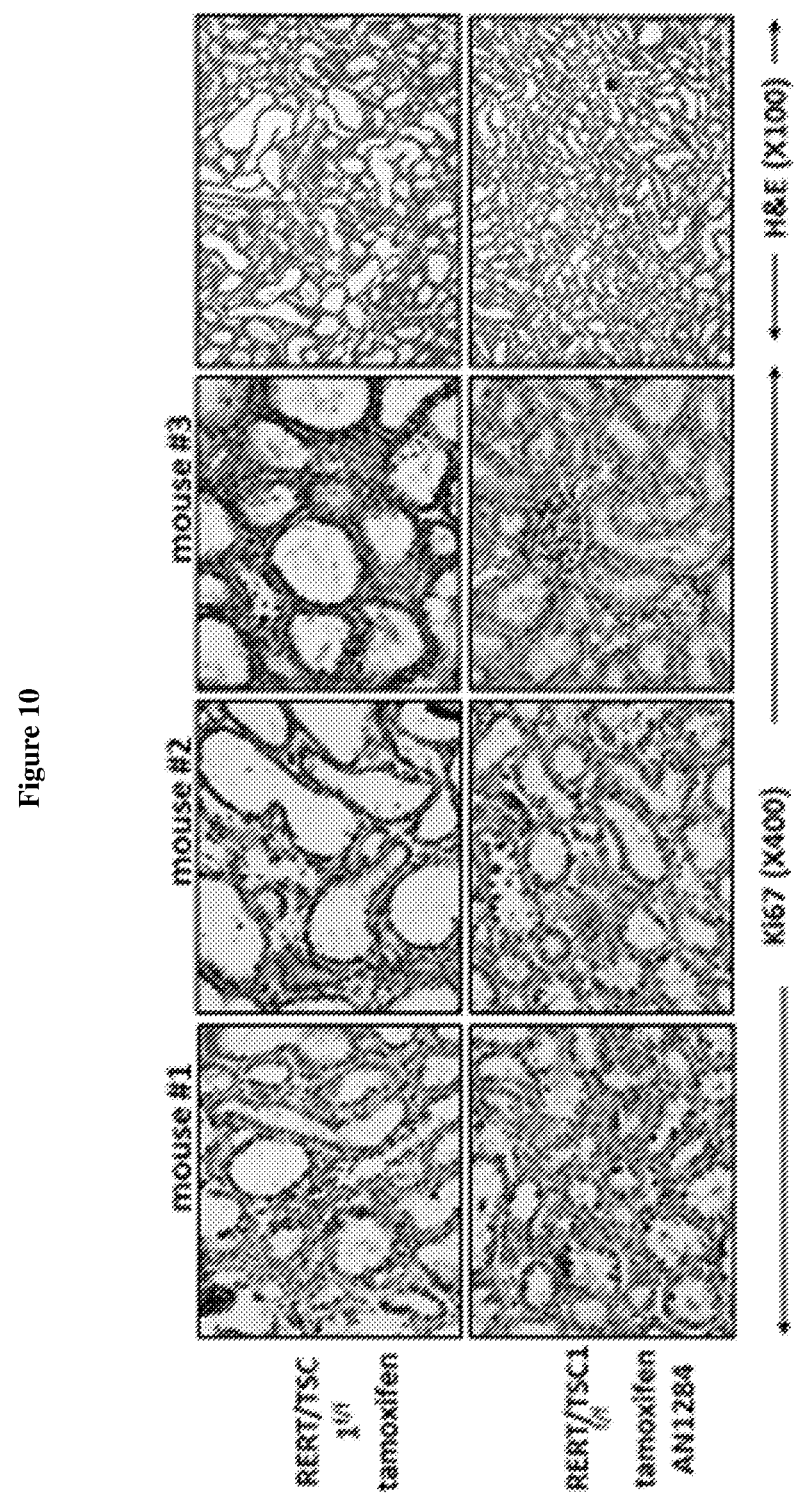

The kidneys of AN1284-treated mice showed a clear reduction in renal cysts and retention of the aligning columnar epithelial cells in the cyst, while these were missing in those of the mice treated only with tamoxifen. There was also a 50-60% reduction in the number of Ki67-positive cells proliferating cells following drug treatment. The data indicate that the treatment with AN1284 is effective in reducing the kidney pathology associated with TSC1 deletion in the RERT/TSC1$^{f/f}$ model even when initiated at a late stage (FIG. 10).

Figures 11A, 11B, 11C, 11D:
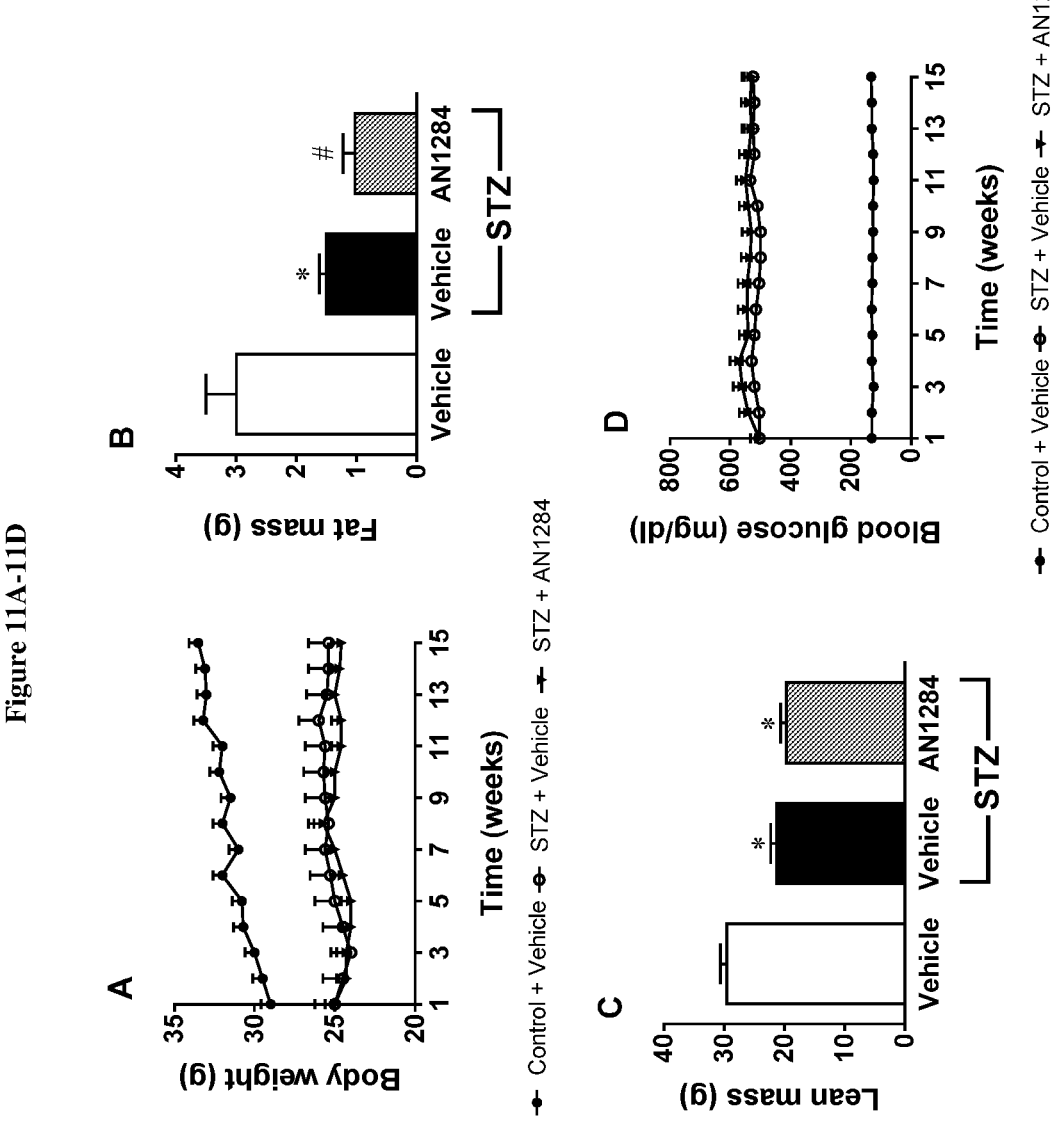
FIGS. 11A-11D shows the reduction of renal damage in type 1 diabetic mice with renal nephropathy-deleted mice treated with AN1284. Change in body weight during the study (FIG. 11A), change in total fat mass (FIG. 11B); change in lean body mass (FIG. 11C), degree of hyperglycaemia (FIG. 11D).
Figure 12A:
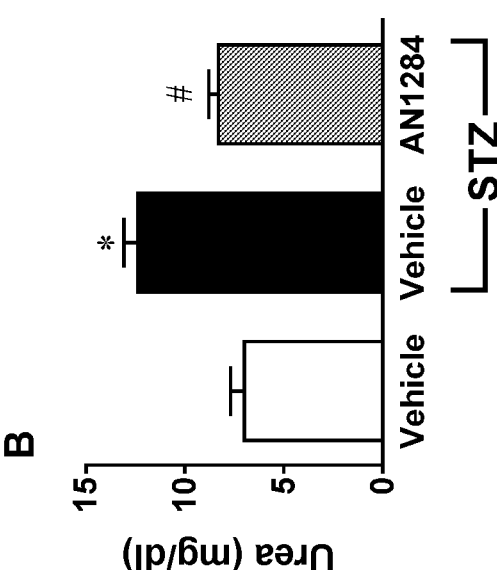
FIGS. 12A-12B shows how AN1284 reduces elevation of albumin and urea in urine of mice with diabetes-induced renal dysfunction.
Figure 12B:
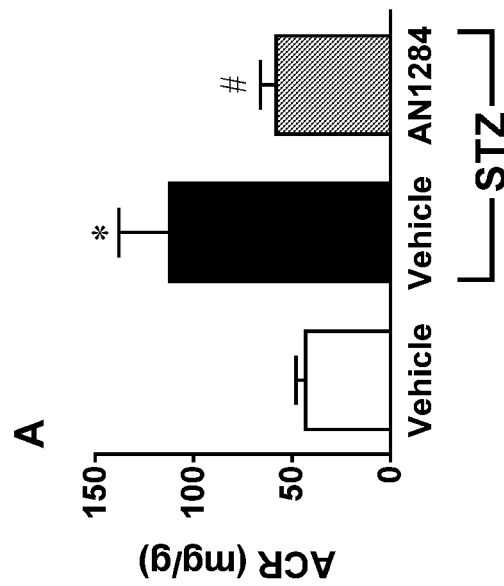
Figures 13A, 13B, 13C:
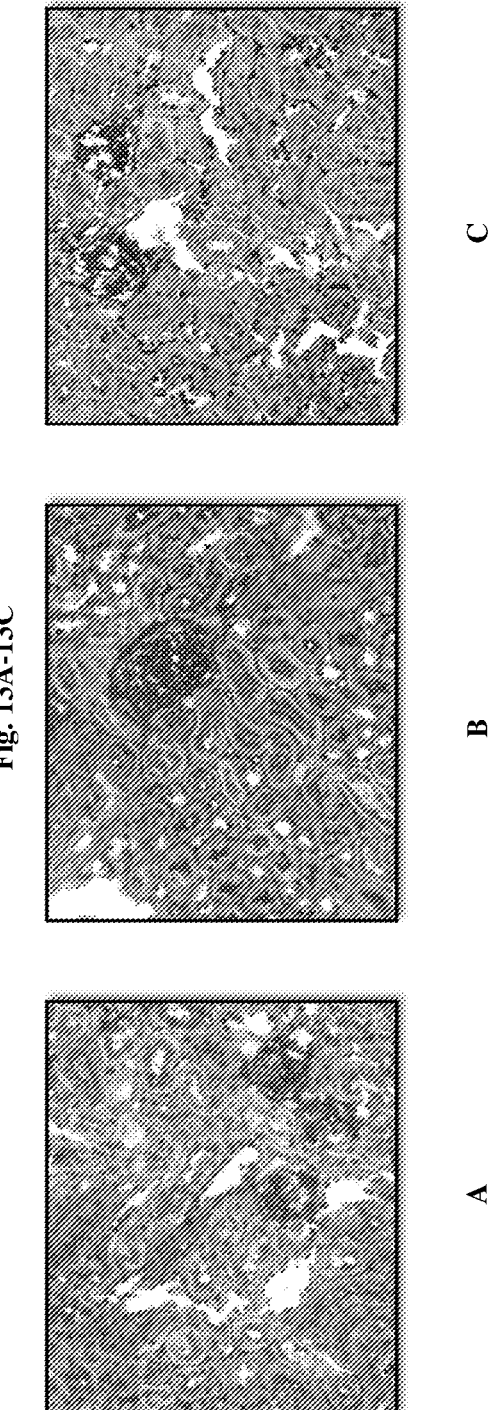
FIGS. 13A-13C shows sections of kidney showing glomerular area.
Figures 14A, 14B:
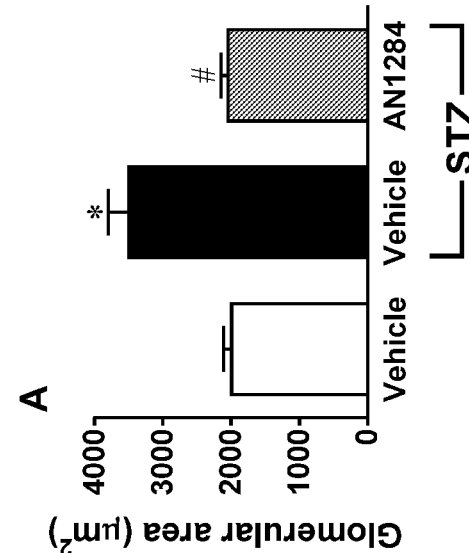
FIG. 14A-14B. Shows reduction by AN1284 of glomerular area and of mesangial expansion in the kidney of mice with diabetes-induced renal dysfunction.
Figures 15A, 15B, 15C, 15D, 15E, 15F:
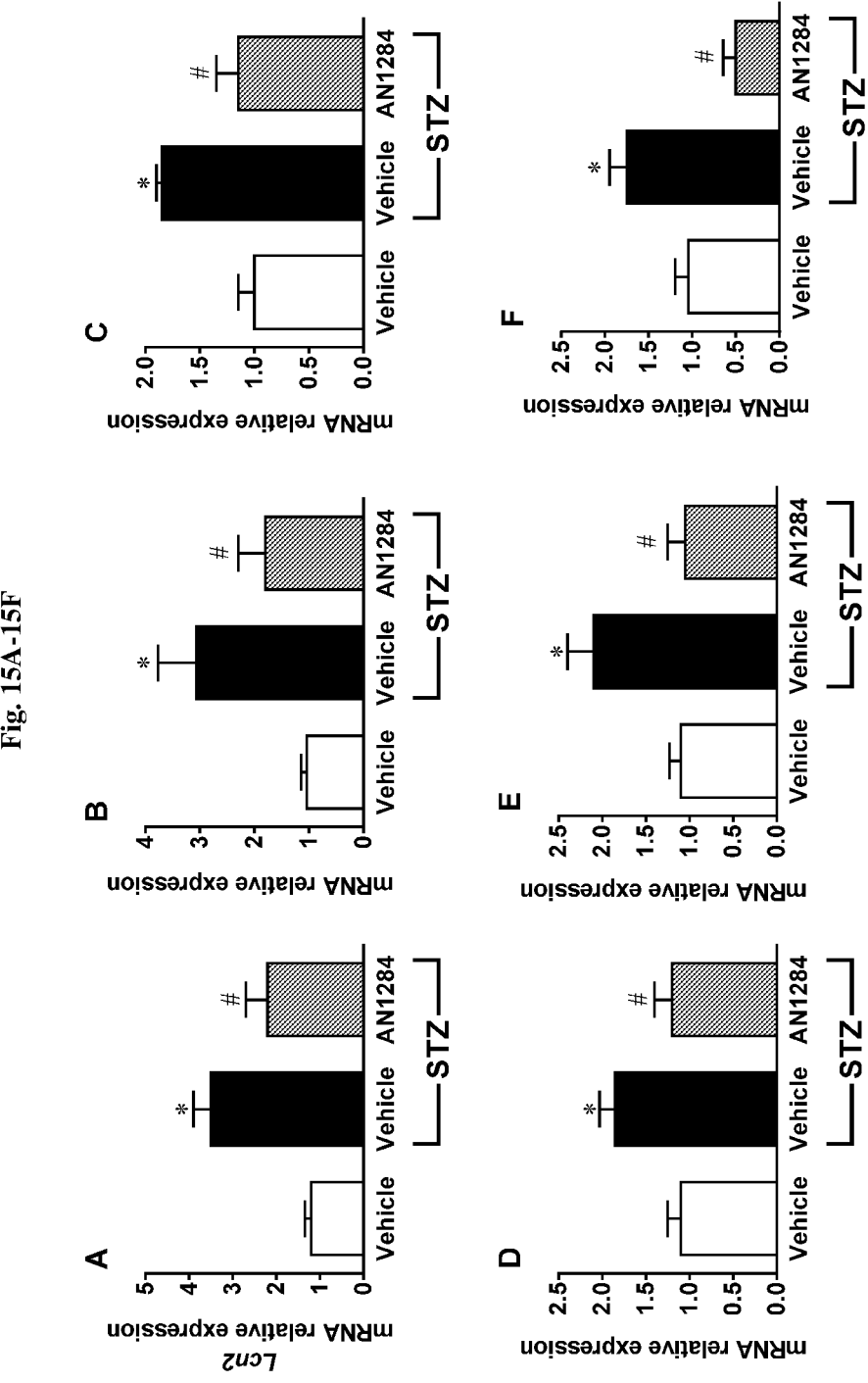

Reduction of Renal Damage in Type 1 Diabetic Mice with Renal Nephropathy-Deleted Mice Compared with the controls, the diabetic mice did not gain appreciable body weight during the study (FIG. 11A). The reduction in body weight was due to a decrease in total fat mass (FIG. 11B) with no change in lean body mass (FIG. 11C). Interestingly, AN1284 induced a further reduction in total fat mass. AN1284 did not affect the degree of hyperglycaemia (FIG. 11D). The kidney-to-body weight ratio which increases in the diabetic-vehicle (Veh)-treated group was significantly reduced by AN1284. Moreover, chronic treatment with AN1284 was effective in normalizing urine albumin-to-creatinine ratio (FIG. 12A) and blood urea nitrogen levels (FIG. 12B), glomerular cross-sectional area (FIG. 13). Compared with nondiabetic control mice, increased glomerular space area and mesangial expansion were noted in the diabetic-vehicle-treated animals, effects that were completely normalised by AN1284 (FIG. 14A-14B). AN1284 also significantly reduced the elevated mRNA expression levels of the kidney injury marker, lipocalin 2, in whole kidney homogenates of diabetic mice (FIG. 15A) and those of collagen-1 (FIG. 15B), collagen-3 (FIG. 15C), TIMP1 (FIG. 15D) and IP-10 (FIG. 15E). These data indicate a robust efficacy of AN1284 for DN in a manner independent of the diabetes itself.

Reduction of Acute Pancreatitis Induced by Cerulein in Mice.

Figure 16A:
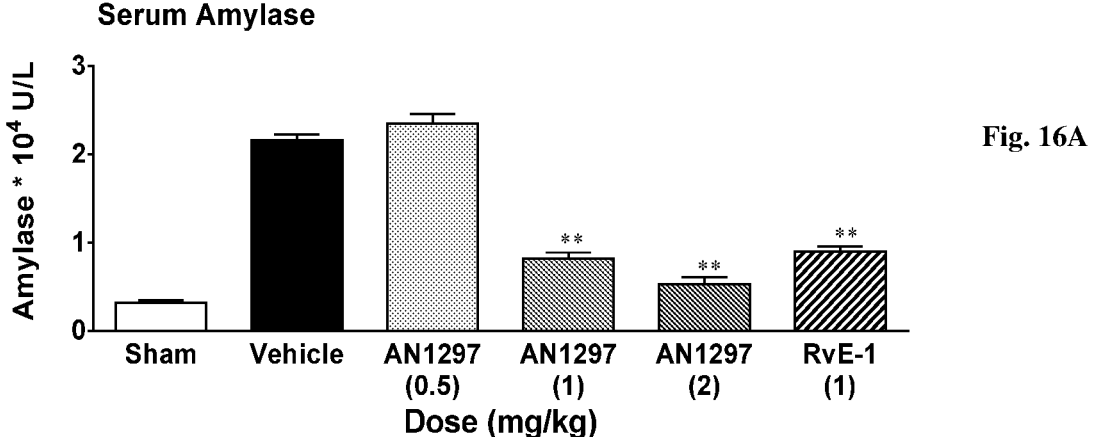
FIGS. 16A-16B shows mitigation of pancreatitis by AN1297. Dose related reduction by AN1927 of serum amylase (FIG. 16A) and B. pancreatic TNF-α (FIG. 16B) in mice with acute pancreatitis induced by cerulean injections. Resolvin-D (RvE) (1 mg/kg) was used as a positive control. Significantly different from untreated mice *, p<0.05 **, p<0.01.
Figure 16B:
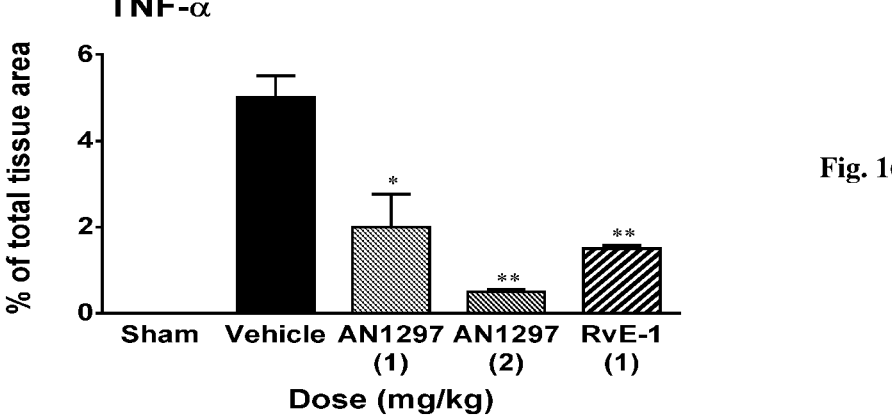

Serum amylase increased 7-fold, following cerulein injections. These were decreased significantly by AN1297 (1 and 2 mg/kg) in a dose dependent manner (FIG. 16A). AN1297 also dose-dependently reduced TNF-α protein in the pancreas (FIG. 16B).

The invention claimed is:

1. The pharmaceutical composition comprising a compound being the active therapeutic agent being selected from:

and any combinations thereof.

* * * * *